(12) United States Patent
Baxter et al.

(10) Patent No.: US 7,776,882 B2
(45) Date of Patent: Aug. 17, 2010

(54) 2-AMINO-3,4-DIHYDRO-QUINOLINE DERIVATIVES USEFUL AS INHIBITORS OF β-SECRETASE (BACE)

(76) Inventors: Ellen W. Baxter, 148 N. Keswick Ave., Glenside, PA (US) 19038; Allen B. Reitz, 109 Greenbriar Rd., Lansdale, PA (US) 19446; Christopher John Creighton, 6427 Salizar Ct., San Diego, CA (US) 92111

( * ) Notice: Subject to any disclaimer, the term of this patent is extended or adjusted under 35 U.S.C. 154(b) by 74 days.

(21) Appl. No.: 11/671,703

(22) Filed: Feb. 6, 2007

(65) Prior Publication Data

US 2007/0232642 A1    Oct. 4, 2007

Related U.S. Application Data

(60) Provisional application No. 60/765,650, filed on Feb. 6, 2006.

(51) Int. Cl.
*A61K 31/44* (2006.01)
*A61P 25/28* (2006.01)
*C07D 215/38* (2006.01)

(52) U.S. Cl. ...................... 514/313; 546/159
(58) Field of Classification Search ........................ None
See application file for complete search history.

(56) References Cited

U.S. PATENT DOCUMENTS

| | | | |
|---|---|---|---|
| 4,001,237 A | 1/1977 | Partyka et al. | |
| 4,675,047 A | 6/1987 | Serban et al. | |
| 4,739,056 A | 4/1988 | Venuti et al. | |
| 4,761,416 A | 8/1988 | Fried et al. | |
| 5,387,742 A | 2/1995 | Cordell | |
| 5,580,003 A | 12/1996 | Malone et al. | |
| 5,612,486 A | 3/1997 | McConlogue et al. | |
| 5,672,805 A | 9/1997 | Neve | |
| 5,720,936 A | 2/1998 | Wadsworth et al. | |
| 5,811,633 A | 9/1998 | Wadsworth et al. | |
| 5,850,003 A | 12/1998 | McLonlogue et al. | |
| 5,877,015 A | 3/1999 | Hardy et al. | |
| 5,877,399 A | 3/1999 | Hsiao et al. | |
| 6,037,521 A | 3/2000 | Sato et al. | |
| 6,071,903 A | 6/2000 | Albright et al. | |
| 6,184,435 B1 | 2/2001 | Benson et al. | |
| 6,187,922 B1 | 2/2001 | Geen et al. | |
| 6,211,428 B1 | 4/2001 | Singh et al. | |
| 6,340,783 B1 | 1/2002 | Snow | |
| 7,531,545 B2 | 5/2009 | Baxter et al. | |
| 2004/0087548 A1* | 5/2004 | Salvati et al. | 514/81 |
| 2004/0209905 A1* | 10/2004 | Kubo et al. | 514/266.3 |
| 2005/0171111 A1* | 8/2005 | Angibaud et al. | 514/249 |
| 2006/0074105 A1* | 4/2006 | Ware et al. | 514/313 |
| 2006/0178383 A1 | 8/2006 | Bischoff et al. | |
| 2009/0227581 A1 | 9/2009 | Baxter et al. | |
| 2009/0227627 A1 | 9/2009 | Baxter et al. | |

FOREIGN PATENT DOCUMENTS

| | | |
|---|---|---|
| EP | 0406958 | 1/1991 |
| EP | 1407774 | 4/2004 |
| JP | 63-196573 | 8/1988 |
| WO | WO 01/38314 | 5/2001 |
| WO | WO 01/38315 | 5/2001 |
| WO | WO 02/100399 | 12/2002 |
| WO | WO 2004/022523 | 3/2004 |
| WO | WO 2004/058686 | 7/2004 |
| WO | WO 2005/049585 | 6/2005 |
| WO | WO 2006/017836 | 2/2006 |
| WO | WO 2006/017844 | 2/2006 |
| WO | WO 2006/024932 | 3/2006 |
| WO | WO 2006/078577 A1 * | 7/2006 |

OTHER PUBLICATIONS

Larner, A.J.: "Secretases as Therapeutic Targets in Alzheimer's Disease: Patents 2000-2004". Expert Opinion On Therapeutic Patents, Ashley Publications, GB, vol. 14, No. 10, 2004, pp. 1403-1420, XP002404250.

Database Caplus Online Chronical Abstracts Service Columbus, Ohio, US Ishikawa, Fumyoshi et al.: Quinazolineactic acid derivatives as platlets aggregation inhibitors; XP00236713.

Kienzle, Frank et al., "1,5-Dihydroimidazoquinazolinones as blood platelet aggregation inhibitors", European Journal of Medicinal Chemistry, 17(6), 547-556.

Webb, Thomas Hand Wilcox, Improved Synthesis of Symmetrical and Unsymmetrical 5,11-methandibenzo'b.f.1,5-diazocines. Readily Available Nanoscale Structural Units, Journal of Organic Chemistry, vol. 55, No. 1, 1990, pp. 363-365.

Venuti, M.C. et al., Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl1-Oxybutyramide J. Medicinal Chemistry, American Chemical Society, vol. 30, No. 2, 1987, pp. 303-318.

Patent Abstracts of Japan, vol. 016, No. 160 (P-1340) Apr. 20, 1992, JP 04 011255 (Fuji Photo Film Co Ltd), Jan. 16, 1992, p. 5, compound 20.

(Continued)

*Primary Examiner*—Brian-Yong S Kwon
*Assistant Examiner*—Bong-Sook Baek

(57) ABSTRACT

The present invention is directed to 2-amino-3,4-dihydro-quinoline derivatives, pharmaceutical compositions containing them and their use in the treatment of Alzheimer's disease (AD) and related disorders. The compounds of the invention are inhibitors of β-secretase, also known as β-site cleaving enzyme and BACE, BACE1, Asp2 and memapsin2.

6 Claims, No Drawings

OTHER PUBLICATIONS

U.S. Appl. No. 11/197,669, Baxter et al.
U.S. Appl. No. 11/197,608, Baxter et al.
U.S. Appl. No. 11/197,615, Baxter et al,.
U.S. Appl. No. 11/197,681, Baxter et al.
U.S. Appl. No. 11/671,732, Baxter et al.
U.S. Appl. No. 11/552,792, Baxter et al.
PCT Search Report PCT/US2007/061691 dated Aug. 14, 2007.
International Search Report re: PCT/US2007/061677 dated Aug. 14, 2007.
Office Action mailed Aug. 21, 2008 in U.S. Appl. No. 11/197,669.
Office Action mailed Apr. 29, 2009 in U.S. Appl. No. 11/197,669.
Office Action mailed May 30, 2008 in U.S. Appl. No. 11/197,608.
Office Action mailed Aug. 20, 2008 in U.S. Appl. No. 11/197,608.
Office Action mailed Apr. 30, 2009 in U.S. Appl. No. 11/197,608.
Office Action mailed May 29, 2008 in U.S. Appl. No. 11/197,615.
Office Action mailed Jan. 27, 2009 in U.S. Appl. No. 11/197,615.
Office Action mailed Jun. 19, 2009 in U.S. Appl. No. 11/671,681.
Office Action mailed Mar. 24, 2009 in U.S. Appl. No. 11/671,732.
Office Action mailed Sep. 10, 2009 in U.S. Appl. No. 12/362,020.
Citron, Trends in Pharm. Sci., vol. 25, Issue 2, Feb. 2004, 92-97.
Cole, et al., Molecular Neurodegeneration 2007, 2:22.
El Mouedden, M. et al., (Johnson & Johnson Pharmaceutical Research and Development, Division of Janssen Pharmaceutica N.V., Turnhoutseweg 30, Beerse, Belg.), Development of a specific ELISA for the quantitative study of amino-terminally truncated beta-amyloid peptides,. Journal of Neuroscience Methods (2005), 145(1-2), pp. 97-105.
Games, D. et al., (Athena Neurosciences, Inc., South San Francisco, CA, USA), Alzheimer-type neuropathology in transgenic mice overexpressing V717F β-amyloid precursor protein, Nature (London) (1995), 373(6514), pp. 523-527 (V717F mice).
Hamaguchi, et al., Cell. Mol. Life Sci. 63 (2006) 1538-1552.
Hsiao, K. et al., (Dep. Neurology, Univ. Minnesota, Minneapolis, MN, USA), Correlative memory deficits, Aβ elevation, and amyloid plaques in transgenic mice, Science (Washington, D. C.) (1996), 274(5284), pp. 99-102 (Tg2576 mice).
Kienzle, F. et. al., Chemical Abstract, 1983, vol. 98, Abstract No. 143363, (or Caplus Accession No. 1983:143363).
Lewczuk, P. et al., (Department of Psychiatry and Psychotherapy, Molecular Neurobiology Lab, University of Erlangen-Nuremberg, Erlangen, Germany), Neurochemical diagnosis of Alzheimer's dementia by CSF Aβ42, Aβ42/Aβ40 ratio and total tau, Neurobiology of Aging (2004), 25(3), pp. 273-281.
Lins, H. et al., (Department of Neurology, Otto-von-Guericke-University, Magdeburg, Germany), Immunoreactivities of amyloid β peptide(1-42) and total τ protein in lumbar cerebrospinal fluid of patients with normal pressure hydrocephalus, Journal of Neural Transmission (2004), 111(3), pp. 273-280.
Neve, R. L. et al., (Dep. Genetics, Harvard Medical School and McLean Hospital, Belmont, MA, USA), Transgenic mice expressing APP-C100 in the brain, Neurobiology of Aging (1996), 17(2), pp. 191-203 (APP-C100 mice).
Oddo, S. et al, (Department of Neurobiology and Behavior, University of California, Irvine, Irvine, CA, USA), Triple-transgenic model of Alzheimer's disease with plaques and tangles: Intracellular Aβ and synaptic dysfunction, Neuron (2003), 39(3), pp. 409-421 (APP Triple Transgenic Mice).
Olsson, a. et al., (Sahlgrenska University Hospital, Experimental Neuroscience Section, Institute of Clinical Neuroscience, Goteborg University, Moelndal, Sweden), Measurement of α- and β-secretase cleaved amyloid precursor protein in cerebrospinal fluid from Alzheimer patients, Experimental Neurology (2003), 183(1), pp. 74-80.
Ruberti et al., (Neuroscience Program, International School for Advanced Studies (SISSA), Trieste, Italy), Phenotypic knockout of nerve growth factor in adult transgenic mice reveals severe deficits in basal forebrain cholinergic neurons, cell death in the spleen, and skeletal muscle dystrophy, Journal of Neuroscience (2000), 20(7), pp. 2589-2601 (AD11 mice).
Schoonenboom, N.S. et al., Amyloid β 38, 40, and 42 species in cerebrospinal fluid: More of the same?, Annals of Neurology (2005), 58(1), pp. 139-142.
Sirinathsinghji, D. J. S. (Merck Sharp and Dohme Research Laboratories, Neuroscience Research Centre, Essex, UK.), Transgenic mouse models of Alzheimer's disease, Biochemical Society Transactions (1998), 26(3), pp. 504-508.
Van Leuven, F. (Experimental Genetics Group, Center for Human Genetics, Flemish Institute for Biotechnology (VIB), K.U.Leuven, Louvain, Belg.), Single and multiple transgenic mice as models for Alzheimer's disease, Progress in Neurobiology (Oxford) (2000), 61(3), pp. 305-312.
Vanderstichele, H. et al., (Innogenetics NV, Ghent, Belg.), Standardization of measurement of β-amyloid(1-42) in cerebrospinal fluid and plasma, Amyloid (2000), 7(4), pp. 245-258.
Wahlund, L.-O. et al., (Karolinska Institute, Section of Geriatric Medicine, Department of Clinical Neuroscience and Family Medicine, Huddinge University Hospital, Stockholm, Sweden), Cerebrospinal fluid biomarkers for disease stage and intensity in cognitively impaired patients, Neuroscience Letters (2003), 339(2), pp. 99-102.
Notice of Allowance mailed Dec. 8, 2009 in U.S. Appl. No. 11/197,669.
Notice of Allowance mailed Dec. 8, 2009 in U.S. Appl. No. 11/197,608.
Office Action mailed Sep. 29, 2009 in U.S. Appl. No. 11/671,681.
Notice of Allowance mailed Sep. 25, 2009 in U.S. Appl. No. 11/671,732.
Notice of Allowance mailed Jan. 6, 2010 in U.S. Appl. No. 11/671,732.
Notice of Allowance mailed Dec. 24, 2009 in U.S. Appl. No. 12/362,020.

* cited by examiner

2-AMINO-3,4-DIHYDRO-QUINOLINE DERIVATIVES USEFUL AS INHIBITORS OF β-SECRETASE (BACE)

CROSS REFERENCE TO RELATED APPLICATIONS

This application claims the benefit of U.S. Provisional Application 60/765,650, filed on Feb. 6, 2006, which is incorporated by reference herein in its entirety.

FIELD OF THE INVENTION

The present invention is directed to 2-amino-3,4-dihydroquinoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of β-amyloid$_{1-42}$ (Aβ$_{1-42}$) peptide. Aβ$_{1-42}$ forms oligomers and then fibrils, and ultimately amyloid plaques. The oligomers and fibrils are believed to be especially neurotoxic and may cause most of the neurological damage associated with AD. Agents that prevent the formation of Aβ$_{1-42}$ have the potential to be disease-modifying agents for the treatment of AD. Aβ$_{1-42}$ is generated from the amyloid precursor protein (APP), comprised of 770 amino acids. The N-terminus of Aβ$_{1-42}$ is cleaved by β-secretase (BACE), and then γ-secretase cleaves the C-terminal end. In addition to Aβ$_{1-42}$, γ-secretase also liberates Aβ$_{1-40}$ which is the predominant cleavage product as well as Aβ$_{1-38}$ and Aβ$_{1-43}$. Thus, inhibitors of BACE would be expected to prevent the formation of Aβ$_{1-42}$ as well as Aβ$_{1-40}$, Aβ$_{1-38}$ and Aβ$_{1-43}$ and would be potential therapeutic agents in the treatment of AD.

SUMMARY OF THE INVENTION

The present invention is directed to a compound of formula (I)

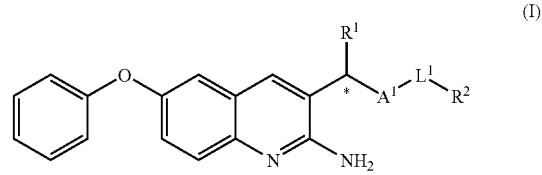

wherein $R^1$ is selected from the group consisting of hydrogen, $C_{1-8}$alkyl, hydroxy substituted $C_{2-8}$alkyl, $NR^AR^B$ substituted —$C_{2-8}$alkyl, —$C_{1-4}$alkyl-O—$C_{1-4}$alkyl, cycloalkyl, —($C_{1-4}$alkyl)-cycloalkyl, heterocycloalkyl and —($C_{1-4}$alkyl)-(heterocycloalkyl); wherein $R^A$ and $R^B$ are each independently selected from the group consisting of hydrogen and $C_{1-4}$alkyl;

provided that when $R^1$ is hydroxy substituted $C_{2-8}$alkyl or $NR^AR^B$ substituted —$C_{2-8}$alkyl, then the hydroxy or $NR^AR^B$ group is not bound to the alpha carbon;

$A^1$ is selected from the group consisting of —$C_{1-4}$alkyl-, —$C_{2-4}$alkenyl- and —$CH_2$-cyclopropyl-;

$L^1$ is selected from the group consisting of —$NR^C$—, —$NR^C$—C(O)— and —C(O)—$NR^C$—; wherein $R^C$ is selected from the group consisting of hydrogen, $C_{1-6}$alkyl, hydroxy substituted $C_{1-4}$alkyl and $C_{5-7}$cycloalkyl;

provided that when $L^1$ is —$NR^C$—, then $A^1$ is —$C_{1-4}$alkyl-;

$R^2$ is selected from the group consisting of $C_{1-8}$alkyl, $C_{2-12}$alkenyl, —$C_{1-4}$alkyl-O—$C_{1-4}$alkyl, —$C_{1-4}$alkyl-$NR^DR^E$, —$C_{1-4}$alkyl-OH, cycloalkyl, —$C_{1-4}$alkyl-cycloalkyl, partially unsaturated carbocyclyl, —$C_{1-4}$alkyl-(partially unsaturated carbocyclyl), aryl, aralkyl, heteroaryl, —$C_{1-4}$alkyl-heteroaryl, heterocycloalkyl, —$C_{1-4}$alkyl-heterocycloalkyl and —CH($R^3$)—$CH_2$—$R^4$;

wherein the cycloalkyl, partially unsaturated carbocyclyl, aryl, heteroaryl or heterocycloalkyl, whether alone or as part of a substituent group, is optionally substituted with one or more substituents independently selected from the group consisting of $C_{1-4}$alkyl, —$C_{1-4}$alkyl-O—$C_{1-4}$alkyl, carboxy, —C(O)O—$C_{1-4}$alkyl and aralkyl;

wherein $R^D$ and $R^E$ are each independently selected from the group consisting of hydrogen and $C_{1-4}$alkyl;

wherein $R^3$ is selected from the group consisting of —$C_{1-4}$alkyl-cycloalkyl, —$CO_2H$, —C(O)O—$C_{1-4}$alkyl and —C(O)—$NR^FR^G$; wherein $R^F$ and $R^G$ are each independently selected from the group consisting of hydrogen and $C_{1-4}$alkyl; alternatively, $R^F$ and $R^G$ are taken together with the nitrogen atom to which they are bound to form a 5 to 6 membered heteroaryl or heterocycloalkyl group;

wherein $R^4$ is selected from the group consisting of hydroxy, $C_{1-4}$alkoxy and benzyl;

alternatively, when $L^1$ is selected from the group consisting of —$NR^C$— and —C(O)—$NR^C$—, $R^C$ and $R^2$ are taken together with the nitrogen atom to which they are bound to form a ring structure selected from the group consisting of 1-piperidinyl, 1-piperazinyl, 4-morpholinyl, 1-pyrrolidinyl, 1-pyrazolidinyl and 1-azepanyl;

wherein the piperidinyl, piperazinyl or morpholinyl is optionally substituted with phenyl; wherein the phenyl is The present invention is further directed to compounds of formula (II)

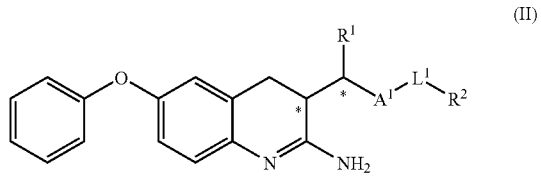

wherein

R¹ is selected from the group consisting of hydrogen, $C_{1-8}$alkyl, hydroxy substituted $C_{2-8}$alkyl, $NR^AR^B$ substituted —$C_{2-8}$alkyl, —$C_{1-4}$alkyl-O—$C_{1-4}$alkyl, cycloalkyl, —($C_{1-4}$ alkyl)-cycloalkyl, heterocycloalkyl and —($C_{1-4}$alkyl)-(heterocycloalkyl); wherein $R^A$ and $R^B$ are each independently selected from the group consisting of hydrogen and $C_{1-4}$alkyl;

provided that when R¹ is hydroxy substituted $C_{2-8}$alkyl or $NR^AR^B$ substituted —$C_{2-8}$alkyl, then the hydroxy or $NR^AR^B$ group is not bound to the alpha carbon;

A¹ is selected from the group consisting of —$C_{1-4}$alkyl-;

L¹ is selected from the group consisting of —$NR^C$—, —$NR^C$—C(O)— and —C(O)—$NR^C$—; wherein $R^C$ is selected from the group consisting of hydrogen, $C_{1-6}$alkyl, hydroxy substituted $C_{1-4}$alkyl and $C_{5-7}$cycloalkyl;

R² is selected from the group consisting of $C_{1-8}$alkyl, $C_{2-12}$alkenyl, —$C_{1-4}$alkyl-O—$C_{1-4}$alkyl, —$C_{1-4}$alkyl-$NR^D$ $R^E$, —$C_{1-4}$alkyl-OH, cycloalkyl, —$C_{1-4}$alkyl-cycloalkyl, partially unsaturated carbocyclyl, —$C_{1-4}$alkyl-(partially unsaturated carbocyclyl), aryl, aralkyl, heteroaryl, —$C_{1-4}$ alkyl-heteroaryl, heterocycloalkyl, —$C_{1-4}$alkyl-heterocycloalkyl and —CH($R^3$)—$CH_2$—$R^4$;

wherein the cycloalkyl, partially unsaturated carbocyclyl, aryl, heteroaryl or heterocycloalkyl, whether alone or as part of a substituent group, is optionally substituted with one or more substituents independently selected from the group consisting of $C_{1-4}$alkyl, —$C_{1-4}$alkyl-O—$C_{1-4}$alkyl, carboxy, —C(O)O—$C_{1-4}$alkyl and aralkyl;

wherein $R^D$ and $R^E$ are each independently selected from the group consisting of hydrogen and $C_{1-4}$alkyl;

wherein R³ is selected from the group consisting of —$C_{1-4}$ alkyl-cycloalkyl, —$CO_2H$, —C(O)O—$C_{1-4}$alkyl and —C(O)—$NR^FR^G$; wherein $R^F$ and $R^G$ are each independently selected from the group consisting of hydrogen and $C_{1-4}$alkyl; alternatively, $R^F$ and $R^G$ are taken together with the nitrogen atom to which they are bound to form a 5 to 6 membered heteroaryl or heterocycloalkyl group;

wherein R⁴ is selected from the group consisting of hydroxy and $C_{1-4}$alkoxy;

alternatively, when L¹ is selected from the group consisting of —$NR^C$— and —C(O)—$NR^C$—, $R^C$ and R² are taken together with the nitrogen atom to which they are bound to form a ring structure selected from the group consisting of 1-piperidinyl, 1-piperazinyl, 4-morpholinyl, 1-pyrrolidinyl, 1-pyrazolidinyl and 1-azepanyl;

wherein the piperidinyl, piperazinyl or morpholinyl is optionally substituted with one or more substituents independently selected from $C_{1-4}$alkyl or —$C_{1-3}$alkyl-C(O)—$NR^J$ $R^K$; wherein $R^J$ and $R^K$ are each independently selected form hydrogen or $C_{1-4}$alkyl; alternatively, $R^J$ and $R^K$ are taken together with the nitrogen atom to which they are bound to form a heteroaryl or heterocycloalkyl;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme, comprising administering to a subject in need thereof a therapeutically effective amount of any of the compounds or pharmaceutical compositions described above.

Further exemplifying the invention are methods of inhibiting the β-secretase enzyme, comprising administering to a subject in need thereof a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I) and compounds of formula (II)

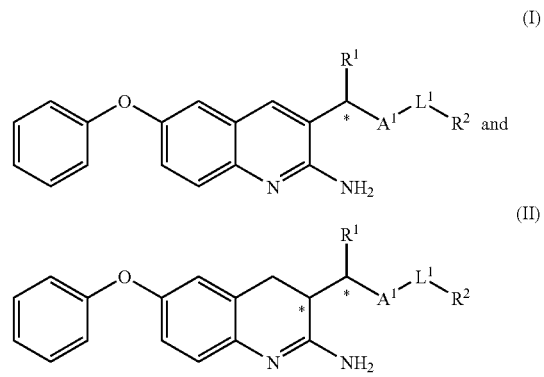

wherein R¹, A¹, L¹ and R² are as herein defined. The compounds of formula (I) and formula (II) are inhibitors of the β-secretase enzyme (also known as β-site cleaving enzyme, BACE, BACE1, Asp2 or memapsin2), and are useful in the treatment of Alzheimer's disease (AD), mild cognitive impairment (MCI), senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, $R^1$ is selected from the group consisting of hydrogen, $C_{1-4}$alkyl, hydroxy substituted $C_{2-4}$alkyl, $NR^A R^B$ substituted —$C_{2-4}$alkyl, cycloalkyl, heterocycloalkyl, —($C_{1-2}$alkyl)-cycloalkyl and —($C_{1-2}$alkyl)-heterocycloalkyl; wherein $R^A$ and $R^B$ are each independently selected from the group consisting of hydrogen and $C_{1-2}$alkyl.

In another embodiment of the present invention, $R^1$ is selected from the group consisting of hydrogen, $C_{1-4}$alkyl, hydroxy substituted $C_{2-4}$alkyl, $NR^A R^B$ substituted —$C_{2-4}$alkyl, —$C_{1-2}$alkyl-O—$C_{1-4}$alkyl, $C_{5-7}$cycloalkyl, 5 to 7 membered heterocycloalkyl, —($C_{1-2}$alkyl)-($C_{5-7}$cycloalkyl) and —($C_{1-2}$alkyl)-(5 to 7 membered heterocycloalkyl); wherein $R^A$ and $R^B$ are each independently selected from the group consisting of hydrogen and $C_{1-2}$alkyl.

In another embodiment of the present invention, $R^1$ is selected from the group consisting of hydrogen, $C_{5-7}$cycloalkyl and 5- to 7-membered heterocycloalkyl.

In an embodiment of the present invention, $R^1$ is selected from the group consisting of hydrogen, cyclohexyl and 4-tetrahydropyranyl. In another embodiment of the present invention, $R^1$ is selected from the group consisting of cyclohexyl, (S)-cyclohexyl, (R)-cyclohexyl and 4-tetrahydropyranyl. In another embodiment of the present invention, $R^1$ is selected from the group consisting of hydrogen, cyclohexyl, (R)-cyclohexyl, (S)-cyclohexyl, 4-tetrahydropyranyl, (R)-4-tetrahydropyranyl and (S)-4-tetrahydropyranyl. In another embodiment of the present invention, $R^1$ is hydrogen.

In an embodiment of the present invention, $A^1$ is selected form the group consisting of —$C_{1-4}$alkyl-, —$C_{2-4}$alkenyl- and —$CH_2$-cyclopropyl-. In another embodiment of the present invention, $A^1$ is selected from the group consisting of —$CH_2$—, —$CH_2CH_2$—, —$CH_2CH_2CH_2$—, —$CH_2CH_2CH_2CH_2$—, —CH=CH—, —$CH_2CH_2$—CH=CH— and —$CH_2$-(1,2-cyclopropyl)-.

In an embodiment of the present invention, $A^1$ is selected from the group consisting of —$C_{1-3}$alkyl-. In another embodiment of the present invention, $A^1$ is selected from the group consisting of —$CH_2$— and —$CH_2CH_2$—. In another embodiment of the present invention, $A^1$ is selected from the group consisting of —$CH_2CH_2$— and —$CH_2CH_2CH_2$—. In another embodiment of the present invention, $A^1$ is —$CH_2$—.

In an embodiment of the present invention, $L^1$ is selected from the group consisting of —$NR^C$—C(O)— and —C(O)—$NR^C$—; wherein $R^C$ is selected from the group consisting of hydrogen, $C_{1-6}$alkyl, hydroxy substituted $C_{1-4}$alkyl and $C_{5-7}$cycloalkyl. In another embodiment of the present invention, $L^1$ is selected from the group consisting of —$NR^C$—C(O)— and —C(O)—$NR^C$—; wherein $R^C$ is selected from the group consisting of hydrogen, $C_{1-4}$alkyl and $C_{5-7}$cycloalkyl.

In another embodiment of the present invention, $L^1$ is selected from the group consisting of —NH—C(O)—, —C(O)—NH—, —C(O)—N(CH$_3$)—, —C(O)—N(n-propyl)-, —C(O)—N(CH$_2$—C(CH$_3$)$_3$)—, —C(O)—N (CH$_2$CH$_2$—C(CH$_3$)$_3$)—, —C(O)—N(CH$_2$CH$_2$—OH)— and —C(O)—N(cyclohexyl)-. In another embodiment of the present invention, $L^1$ is selected from the group consisting of —C(O)—NH—, —C(O)—N(CH$_3$)— and —C(O)—N(cyclohexyl)-. In another embodiment of the present invention, $L^1$ is selected from the group consisting of —C(O)—N (CH$_3$)—, —C(O)—NH—, and —NH—C(O)—. In another embodiment of the present invention, $L^1$ is selected from the group consisting of —C(O)—NH— and —C(O)—N (CH$_3$)—.

In an embodiment of the present invention, $R^2$ is selected from the group consisting of $C_{1-8}$alkyl, $C_{2-12}$alkenyl, —$C_{1-4}$alkyl-O—$C_{1-4}$alkyl, —$C_{1-4}$alkyl-$NR^D R^E$, —$C_{1-4}$alkyl-OH, cycloalkyl, —$C_{1-4}$alkyl-cycloalkyl, partially unsaturated carbocyclyl, —$C_{1-4}$alkyl-(partially unsaturated carbocyclyl), aryl, aralkyl, heteroaryl, —$C_{1-4}$alkyl-heteroaryl, heterocycloalkyl, —$C_{1-4}$alkyl-heterocycloalkyl and —CH($R^3$)—CH$_2$—$R^4$; wherein the cycloalkyl, aryl, heteroaryl or heterocycloalkyl, whether alone or as part of a substituent group, is optionally substituted with one to two substituents independently selected from the group consisting of $C_{1-4}$alkyl, —$C_{1-4}$alkyl-O—$C_{1-4}$alkyl, carboxy, —C(O)O—$C_{1-4}$alkyl and aralkyl; and wherein $R^D$ and $R^E$ are each independently selected from the group consisting of hydrogen and $C_{1-4}$alkyl.

In another embodiment of the present invention, $R^2$ is selected from the group consisting of $C_{1-8}$alkyl, $C_{2-12}$alkenyl, $C_{1-4}$alkyl-OH, $C_{1-4}$alkyl-$NR^D R^E$, —$C_{1-4}$alkyl-O—$C_{1-4}$alkyl, cycloalkyl, cycloalkyl-$C_{1-4}$alkyl-, aralkyl, heterocycloalkyl, heterocycloalkyl-$C_{1-4}$alkyl-, heteroaryl, heteroaryl-$C_{1-4}$alkyl- and —CH($R^3$)—CH$_2$—$R^4$; wherein the cycloalkyl, heteroaryl or heterocycloalkyl, whether alone or as part of a substituent group is optionally substituted with one to two substituents independently selected from the group consisting of carboxy, $C_{1-4}$alkyl, —C(O)—O—$C_{1-4}$alkyl and aralkyl; and wherein $R^D$ and $R^E$ are each independently selected from hydrogen, methyl or ethyl.

In another embodiment of the present invention, $R^2$ is selected from the group consisting of n-butyl, 3-methyl-n-butyl, 1-(3,7-dimethyl-octa-2,6-dienyl), 1-(2-hydroxy-ethyl), cyclohexyl, 3-methyl-cyclohexyl, cis-1-(4-methoxy-carbonyl-cyclohexyl), trans-1-(4-methoxy-carbonyl-cyclohexyl), cis-1-(4-carboxy-cyclohexyl), trans-1-(4-carboxy-cyclohexyl), adamantyl, cyclopropyl-methyl-, cyclohexyl-methyl-, 1-cyclohexenyl-ethyl-, benzyl, 3-(R)-1-aza-bicyclo[2.2.2]octanyl, 3-(S)-1-aza-bicyclo[2.2.2]octanyl, 2-imidazolyl, 4-morpholinyl-ethyl-, 1-pyrrolidinyl-methyl-, 1-pyrrolidinyl-ethyl-, 2-pyridyl-methyl-, 2-imidazolyl-methyl-, 4-imidazolyl-methyl-, 2-(1-methyl-imidazolyl)-methyl-, 5-(1-benzyl-1,2,3,4-tetrazolyl)-methyl-, methoxy-ethyl-, 2-(t-butoxy)-ethyl-, diethylamino-ethyl-, 1-(2-(R)-methoxy-ethyl)-pyrrolidinyl), (S)-(1-cyclohexyl methyl)-2-hydroxy-ethyl-, (R)-1-(methoxy-carbonyl)-2-t-butoxy-ethyl, (R)-1-(methoxy-carbonyl)-2-hydroxy-ethyl, (R)-1-carboxy-2-t-butoxy-ethyl-, (R)-1-(4-morpholinyl-carbonyl)-2-t-butoxy-ethyl- and (R)-1-(amino-carbonyl)-2-t-butoxy-ethyl-.

In another embodiment of the present invention, $R^2$ is selected from the group consisting of 1-(2-hydroxy-ethyl), 2-(t-butoxy)-ethyl, cyclohexyl, cyclopropyl-methyl-, cyclopropyl-methyl-, 2-imidazolyl, 2-imidazolyl-methyl-, 4-imidazolyl-methyl-, 2-(1-methyl-imidazolyl)-methyl-, 5-(1-benzyl-1,2,3,4-tetrazolyl)-methyl-, 1-pyrrolidinyl-methyl-, 2-pyridyl-methyl-, 4-morpholinyl-ethyl-, 3-(R)-1-aza-bicyclo[2.2.2]octanyl, (R)-1-(4-morpholinyl-carbonyl)-2-t-butoxy-ethyl-. In another embodiment of the present invention, $R^2$ is selected from the group consisting of cyclohexyl, 3-methyl-cyclohexyl, adamantyl and 1-(3,7-dimethyl-octa-2,6-dienyl).

In an embodiment of the present invention, $R^2$ is selected from the group consisting of $C_{1-8}$alkyl, $C_{2-12}$alkenyl, —$C_{1-4}$alkyl-$NR^D R^E$, cycloalkyl, —$C_{1-4}$alkyl-cycloalkyl, heterocycloalkyl and —$C_{1-4}$alkyl-heterocycloalkyl; wherein the cycloalkyl or heterocycloalkyl, whether alone or as part of a substituent group, is optionally substituted with one to two substituents independently selected from the group consisting of $C_{1-4}$alkyl, —$C_{1-4}$alkyl-O—$C_{1-4}$alkyl, carboxy and —C(O)O—$C_{1-4}$alkyl; and wherein $R^D$ and $R^E$ are each independently selected from the group consisting of hydrogen and $C_{1-2}$alkyl.

In another embodiment of the present invention, $R^2$ is selected from the group consisting of $C_{1-4}$alkyl, cycloalkyl and 5 to 7 membered heterocycloalkyl; wherein the heterocycloalkyl is optionally substituted with a substituent selected from $C_{1-4}$alkyl.

In another embodiment of the present invention, $R^2$ is selected from the group consisting of t-butyl, cyclohexyl, 2-adamantyl and 4-(1-methyl-piperidinyl).

In an embodiment of the present invention, $R^3$ is selected from the group consisting of —$C_{1-4}$alkyl-cycloalkyl, —$CO_2H$, —C(O)O—$C_{1-4}$alkyl and —C(O)—$NR^F R^G$; wherein $R^F$ and $R^G$ are each independently selected from the group consisting of hydrogen and $C_{1-4}$alkyl; alternatively, $R^F$ and $R^G$ are taken together with the nitrogen atom to which they are bound to form a 5 to 6 membered heterocycloalkyl group.

In another embodiment of the present invention, $R^3$ is selected from the group consisting of —$C_{1-4}$alkyl-cycloalkyl, —$CO_2H$, —C(O)O—$C_{1-4}$alkyl and —C(O)—$NR^F R^G$; wherein $R^F$ and $R^G$ are each independently selected from the group consisting of hydrogen, methyl and ethyl; alternatively, $R^F$ and $R^G$ are taken together with the nitrogen atom to which they are bound to form a 5 to 6 membered saturated heterocycloalkyl group. In another embodiment of the present invention, $R^3$ is selected from the group consisting of cyclohexyl-methyl-, carboxy, methoxy-carbonyl-, amino-carbonyl- and 4-morpholinyl-carbonyl-.

In an embodiment of the present invention, $R^4$ is selected from the group consisting of hydroxy and $C_{1-4}$alkoxy. In another embodiment of the present invention, $R^4$ is selected from the group consisting of hydroxy and t-butoxy.

In an embodiment of the present invention, $L^1$ is selected from the group consisting of —$NR^C$— and —C(O)—$NR^C$—; and $R^C$ and $R^2$ are taken together with the nitrogen atom to which they are bound to form a ring structure selected from the group consisting of 1-piperidinyl, 1-piperazinyl and 4-morpholinyl; wherein the piperidinyl, piperazinyl or morpholinyl is optionally substituted with phenyl; and wherein the phenyl is optionally substituted with one to two substituents independently selected from the group consisting of halogen and $C_{1-4}$alkyl.

In another embodiment of the present invention, $L^1$ is —C(O)—$NR^C$—; and $R^C$ and $R^2$ are taken together with the nitrogen atom to which they are bound to form a ring structure selected from the group consisting of 1-piperidinyl and 1-piperazinyl; wherein the piperidinyl or piperazinyl is optionally substituted with phenyl; wherein the phenyl is optionally substituted with one substituent independently selected from the group consisting of halogen and $C_{1-2}$alkyl.

In another embodiment of the present invention, $L^1$ is —C(O)—$NR^C$—; and $R^C$ and $R^2$ are taken together with the nitrogen atom to which they are bound to form 1-(4-(2-methylphenyl))-piperazinyl or 1-(4-(3-fluorophenyl))-piperazinyl.

In an embodiment of the present invention, $L^1$ is —C(O)—$N(R^C)$—; and $R^C$ and $R^2$ are taken together with the nitrogen atom to which they are bound to form a ring structure selected from the group consisting of 1-piperidinyl, 1-piperazinyl and 4-morpholinyl; wherein the piperidinyl, piperazinyl or morpholinyl is optionally substituted with —$C_{1-3}$alkyl-C(O)—$NR^J R^K$; wherein $R^J$ and $R^K$ are each independently selected form hydrogen or $C_{1-4}$alkyl; alternatively, $R^J$ and $R^K$ are taken together with the nitrogen atom to which they are bound to form a 5-7 membered heterocycloalkyl.

In another embodiment of the present invention, $L^1$ is —C(O)—$N(R^C)$—; and $R^C$ and $R^2$ are taken together with the nitrogen atom to which they are bound to form a ring structure selected from the group consisting of 1-piperidinyl and 1-piperazinyl; wherein the piperidinyl or piperazinyl is optionally substituted with —$C_{1-3}$alkyl-C(O)—$NR^J R^K$; wherein $R^J$ and $R^K$ are each independently selected form hydrogen or $C_{1-4}$alkyl; alternatively, $R^J$ and $R^K$ are taken together with the nitrogen atom to which they are bound to form a 5-7 membered heterocycloalkyl.

In another embodiment of the present invention, $L^1$ is —C(O)—$N(R^C)$—; and $R^C$ and $R^2$ are taken together with the nitrogen atom to which they are bound to form 1-(4-morpholinyl-carbonyl-methyl)-piperazinyl.

In an embodiment of the present invention, wherein $L^1$ is —$NR^C$— or —$NR^C$—C(O)— and $R^2$ is —$C_{2-4}$alkenyl-, preferably, the double bond of the —$C_{2-4}$alkenyl- is not bound directly to the nitrogen atom of the $L^1$ group. In another embodiment of the present invention, $R^2$ is —$C_{3-4}$alkenyl, preferably, 2-propenyl.

Additional embodiments of the present invention are directed to any single or subset of compounds of formula (I) and/or compounds of formula (II) selected from the group consisting of the compounds listed in Tables 1-4, below.

Additional embodiments of the present invention, include those wherein the substituents selected for one or more of the variables defined herein (e.g. $R^1$, $R^2$, $A^1$, $L^1$, etc.) are independently selected to be any individual substituent or any subset of substituents selected from the complete list as defined herein. Additional embodiments of the present invention, include those wherein the substituents selected for one or more of the variables defined herein (e.g. $R^1$, $R^2$, $A^1$, $L^1$, etc.) are independently selected to be any individual substituent or any subset of substituents listed in Table 1-5 below.

Representative compounds of the present invention are as listed in Tables 1 through 4, below. Unless otherwise noted, all compounds were prepared as mixtures of stereo-isomers. For substituent groups bound through two points in the structures in the Tables below, for example the $L^1$ group, the substituent group is identified as it would be incorporated into the structure heading the table.

TABLE 1

Representative compounds of formula (I)

| ID No | R¹ | A¹ | L¹ | R² |
|---|---|---|---|---|
| 1 | H | —CH₂— | —C(O)—N(CH₃)— | cyclohexyl |
| 2 | H | —CH₂— | —C(O)NH— | adamantyl |
| 3 | H | —CH₂— | —C(O)NH— | 3-methyl-cyclohexyl |
| 4 | H | —CH₂— | —NHC(O)— | cyclohexyl |
| 5 | H | —CH₂— | —C(O)NH— | methoxy-ethyl- |
| 6 | H | —CH₂— | —C(O)NH— | 1-(2-(R)-methoxy-ethyl)-pyrrolidinyl) |
| 7 | H | —CH₂— | —C(O)N(n-propyl)- | cyclopropyl-methyl- |
| 8 | H | —CH₂— | —C(O)NH— | 1-cyclohexenyl-ethyl- |
| 9 | H | —CH₂— | —C(O)NH— | 1-3-methyl-n-butyl |
| 10 | H | —CH₂— | —C(O)NH— | diethylamino-ethyl- |
| 11 | H | —CH₂— | —C(O)NH— | cyclohexyl-methyl |
| 12 | H | —CH₂— | —C(O)NH— | n-butyl |
| 13 | H | —CH₂— | —C(O)NH— | 1-(3,7-dimethyl-octa-2,6-dienyl) |
| 14 | H | —CH₂— | —C(O)NH— | (S)-(1-cyclohexylmethyl)-2-hydroxy-ethyl |
| 15 | cyclohexyl | —CH₂CH₂— | —C(O)NH— | adamantyl |
| 16 | cyclohexyl | —CH₂CH₂— | —C(O)—N(CH₃)— | cyclohexyl |
| 17 | H | —CH₂CH₂— | —C(O)NH— | adamantyl |
| 18 | H | —CH₂CH₂— | —C(O)—N(CH₃)— | cyclohexyl |
| 19 | cyclohexyl | —CH₂CH₂— | —C(O)NH— | cis-1-(4-methoxy-carbonyl-cyclohexyl) |
| 20 | cyclohexyl | —CH₂CH₂— | —C(O)NH— | trans-1-(4-methoxy-carbonyl-cyclohexyl) |
| 21 | cyclohexyl | —CH₂CH₂— | —C(O)NH— | cis-1-(4-carboxy-cyclohexyl) |
| 22 | cyclohexyl | —CH₂CH₂— | —C(O)NH— | trans-1-(4-carboxy-cyclohexyl) |
| 23 | 4-tetrahydro-pyranyl | —CH₂CH₂— | —C(O)—N(CH₃)— | cyclohexyl |
| 24 | 4-tetrahydro-pyranyl | —CH₂CH₂— | —C(O)NH— | adamantyl |
| 25 | (S)-4-tetrahydro-pyranyl | —CH₂CH₂— | —C(O)—N(CH₃)— | cyclohexyl |
| 26 | (R)-4-tetrahydro-pyranyl | —CH₂CH₂— | —C(O)—N(CH₃)— | cyclohexyl |
| 27 | 4-tetrahydro-pyranyl | —CH₂CH₂— | —C(O)NH— | (R)-1-(methoxy-carbonyl)-2-t-butoxy-ethyl |
| 28 | (R)-4-tetrahydro-pyranyl | —CH₂CH₂— | —C(O)NH— | (R)-1-carboxy-2-t-butoxy-ethyl |
| 29 | (S)-4-tetrahydro-pyranyl | —CH₂CH₂— | —C(O)NH— | (R)-1-carboxy-2-t-butoxy-ethyl |
| 30 | 4-tetrahydro-pyranyl | —CH₂CH₂— | —C(O)—N(cyclohexyl)- | 2-imidazolyl-methyl- |
| 31 | 4-tetrahydro-pyranyl | —CH₂CH₂— | —C(O)NH— | 5-(1-benzyl-1,2,3,4-tetrazolyl)-methyl- |
| 32 | 4-tetrahydro-pyranyl | —CH₂CH₂—CH=CH— | —C(O)—N(CH₃)— | cyclohexyl |
| 33 | 4-tetrahydro-pyranyl | —CH₂CH₂—CH₂CH₂— | —C(O)—N(CH₃)— | cyclohexyl |
| 34 | 4-tetrahydro-pyranyl | —CH₂CH₂—CH=CH— | —C(O)NH— | (R)-1-(methoxy-carbonyl)-2-t-butoxy-ethyl |
| 35 | 4-tetrahydro-pyranyl | —CH₂CH₂—CH=CH— | —C(O)NH— | (R)-1-(methoxy-carbonyl)-2-hydroxy-ethyl |
| 36 | 4-tetrahydro-pyranyl | —CH₂CH₂— | —C(O)NH— | cyclopropyl-methyl- |
| 37 | cyclohexyl | —CH₂CH₂— | —C(O)—N(cyclohexyl)- | 1-pyrrolidinyl-ethyl- |

TABLE 1-continued

Representative compounds of formula (I)

| ID No | R$^1$ | A$^1$ | L$^1$ | R$^2$ |
|---|---|---|---|---|
| 38 | cyclohexyl | —CH$_2$CH$_2$— | —C(O)—N(CH$_3$)— | benzyl |
| 39 | cyclohexyl | —CH$_2$CH$_2$— | —C(O)—N(cyclohexyl)- | 2-(1-methyl-imidazolyl)-methyl- |
| 40 | cyclohexyl | —CH$_2$CH$_2$CH$_2$— | —C(O)—N(CH$_3$)— | cyclohexyl |
| 41 | cyclohexyl | —CH$_2$CH$_2$— | —C(O)—N(cyclohexyl)- | 2-imidazolyl |
| 42 | cyclohexyl | —CH$_2$CH$_2$— | —C(O)—N(cyclohexyl)- | 1-(2-hydroxy-ethyl) |
| 43 | cyclohexyl | —CH$_2$CH$_2$— | —C(O)—N(CH$_2$—C(CH$_3$)$_3$)— | 2-(1-methyl-imidazolyl)-methyl- |
| 44 | (R)-cyclohexyl | —CH$_2$CH$_2$— | —C(O)—NH— | (R)-1-(4-morpholinyl-carbonyl)-2-t-butoxy-ethyl |
| 45 | (S)-cyclohexyl | —CH$_2$CH$_2$— | —C(O)—NH— | (R)-1-(4-morpholinyl-carbonyl)-2-t-butoxy-ethyl |
| 46 | 4-tetrahydro-pyranyl | —CH$_2$CH$_2$CH$_2$— | —C(O)—NH— | (R)-1-(amino-carbonyl)-2-t-butoxy-ethyl |
| 47 | cyclohexyl | —CH$_2$CH$_2$— | —C(O)—N(CH$_3$)— | cyclohexyl-methyl- |
| 48 | (R)-4-tetrahydro-pyranyl | —CH$_2$CH$_2$— | —C(O)—NH— | (R)-1-(4-morpholinyl-carbonyl)-2-t-butoxy-ethyl |
| 49 | (S)-4-tetrahydro-pyranyl | —CH$_2$CH$_2$— | —C(O)—NH— | (R)-1-(4-morpholinyl-carbonyl)-2-t-butoxy-ethyl |
| 50 | 4-tetrahydro-pyranyl | —CH$_2$CH$_2$— | —C(O)—N(cyclohexyl)- | 1-(2-hydroxy-ethyl) |
| 51 | 4-tetrahydro-pyranyl | —CH$_2$CH$_2$— | —C(O)—NH— | 3-(R)-1-aza-bicyclo[2.2.2]octanyl |
| 52 | 4-tetrahydro-pyranyl | —CH$_2$CH$_2$— | —C(O)—NH— | 3-(S)-1-aza-bicyclo[2.2.2]octanyl |
| 53 | 4-tetrahydro-pyranyl | —CH$_2$CH$_2$— | —C(O)—N(cyclohexyl)- | 4-imidazolyl-methyl- |
| 54 | 4-tetrahydro-pyranyl | —CH$_2$CH$_2$— | —C(O)—N(cyclohexyl)- | 2-(1-methyl-imidazolyl)-methyl- |
| 55 | 4-tetrahydro-pyranyl | —CH$_2$CH$_2$— | —C(O)—N(CH$_2$—C(CH$_3$)$_3$)— | 2-(1-methyl-imidazolyl)-methyl- |
| 56 | 4-tetrahydro-pyranyl | —CH$_2$CH$_2$— | —C(O)—N(CH$_2$CH$_2$—C(CH$_3$)$_3$)— | 2-(1-methyl-imidazolyl)-methyl- |
| 57 | 4-tetrahydro-pyranyl | —CH$_2$CH$_2$— | —C(O)—N(CH$_2$CH$_2$—C(CH$_3$)$_3$)— | 2-imidazolyl)-methyl- |
| 58 | 4-tetrahydro-pyranyl | —CH$_2$CH$_2$— | —C(O)—N(CH$_2$—C(CH$_3$)$_3$)— | 2-imidazolyl-methyl- |
| 59 | 4-tetrahydro-pyranyl | —CH$_2$CH$_2$— | —C(O)—N(CH$_2$—C(CH$_3$)$_3$)— | 4-imidazolyl-methyl- |
| 60 | 4-tetrahydro-pyranyl | —CH$_2$CH$_2$— | —C(O)—N(cyclohexyl)- | 2-pyridyl-methyl- |
| 61 | cyclohexyl | —CH$_2$CH$_2$— | —N(CH$_3$)— | cyclohexyl |
| 62 | (R)-cyclohexyl | —CH$_2$—(1,2-cyclopropyl)- | —C(O)—N(CH$_3$)— | cyclohexyl |
| 63 | (S)-cyclohexyl | —CH$_2$—(1,2-cyclopropyl)- | —C(O)—N(CH$_3$)— | cyclohexyl |
| 64 | 4-tetrahydro-pyranyl | —CH$_2$CH$_2$— | —C(O)—N(cyclohexyl)- | 1-pyrrolidinyl-methyl- |
| 65 | 4-tetrahydro-pyranyl | —CH$_2$CH$_2$— | —C(O)—N(cyclohexyl)- | 4-morpholinyl-ethyl- |
| 66 | 4-tetrahydro-pyranyl | —CH$_2$CH$_2$— | —C(O)—N(cyclohexyl)- | 2-(t-butoxy)-ethyl- |
| 67 | 4-tetrahydro-pyranyl | —CH$_2$CH$_2$— | —C(O)—N(cyclohexyl)- | cyclopropyl-methyl- |

TABLE 1-continued

Representative compounds of formula (I)

| ID No | R¹ | A¹ | L¹ | R² |
|---|---|---|---|---|
| 68 | 4-tetrahydro-pyranyl | —CH$_2$CH$_2$— | —C(O)—N(CH$_2$CH$_2$OH)— | cyclopropyl-methyl- |
| 69 | 4-tetrahydro-pyranyl | —CH$_2$CH$_2$— | —C(O)—N(CH$_2$—C(CH$_3$)$_3$)— | 2-pyridyl-methyl- |
| 70 | (R)-cyclohexyl | —CH$_2$CH$_2$— | —C(O)—N(CH$_2$CH$_2$—C(CH$_3$)$_3$)— | 2-(1-methyl-imidazolyl)-methyl- |
| 71 | (S)-cyclohexyl | —CH$_2$CH$_2$— | —C(O)—N(CH$_2$CH$_2$—C(CH$_3$)$_3$)— | 2-(1-methyl-imidazolyl)-methyl- |
| 72 | cyclohexyl | —CH$_2$CH$_2$— | —C(O)—N(CH$_2$CH$_2$—C(CH$_3$)$_3$)— | 2-(1-methyl-imidazolyl)-methyl- |
| 73 | cyclohexyl | -CH=CH— | —C(O)—N(CH$_2$CH$_2$—C(CH$_3$)$_3$)— | 2-(1-methyl-imidazolyl)-methyl- |
| 74 | cyclohexyl | -CH=CH— | —C(O)—N(CH$_3$)— | cyclohexyl |

TABLE 2

Representative Compounds of Formula (I)

| ID No | R¹ | A¹ | NR$^C$R² |
|---|---|---|---|
| 75 | H | —CH$_2$— | 1-(4-(2-methylphenyl)-piperazinyl) |
| 76 | H | —CH$_2$— | 1-(4-(3-fluorophenyl)-piperazinyl) |

TABLE 3

Representative Compounds of Formula (II)

| ID No | Stereo (*) | A¹ | L¹ | R² |
|---|---|---|---|---|
| 101 | Rac | —CH$_2$— | —C(O)—N(CH$_3$)— | cyclohexyl |
| 102 | (S) | —CH$_2$— | —C(O)—N(CH$_3$)— | cyclohexyl |
| 103 | (R) | —CH$_2$— | —C(O)—N(CH$_3$)— | cyclohexyl |
| 104 | Rac | —CH$_2$— | —C(O)—NH— | 2-adamantyl |
| 105 | Rac | —CH$_2$— | —NH—C(O)— | cyclohexyl |
| 106 | Rac | —CH$_2$— | —NH—C(O)— | t-butyl |

TABLE 3-continued

Representative Compounds of Formula (II)

| ID No | Stereo (*) | A¹ | L¹ | R² |
|---|---|---|---|---|
| 107 | Rac | —CH$_2$— | —C(O)—N(CH$_3$)— | 4-(1-methyl-piperidinyl) |

TABLE 4

Representative Compounds of Formula (II)

| ID No. | Stereo (*) | A¹ | NR$^C$R² |
|---|---|---|---|
| 108 | Rac | —CH$_2$— | 1-(4-morpholinyl-carbonyl-methyl)-piperazinyl |

Representative intermediates in the preparation of the compounds of (I) are as listed in Table 5 below.

TABLE 5

Representative Intermediates

| ID No | W | Q |
|---|---|---|
| 500 | —NH$_2$ | —C(O)O-ethyl |
| 501 | —NH$_2$ | -ethyl-C(O)O-t-butyl |
| 502 | —NH$_2$ | -ethyl-C(O)OOH |
| 503 | —NH$_2$ | 1-(1-cyclohexyl-3-butenyl) |
| 504 | —NH$_2$ | -propyl-C(O)O-methyl |
| 505 | —NH$_2$ | 1-(1-(4-tetrahydropyranyl)-4-pentenyl) |
| 506 | —NH$_2$ | 1-(1-(4-tetrahydropyranyl)-3-carboxy-propyl) |
| 507 | —N(C(O)O-t-butyl)$_2$ | 1-(1-(4-tetrahydropyranyl)-3-propenyl) |
| 508 | —NH$_2$ | 1-(1-cyclohexyl-3-(isobutoxy-carbonyl)-propyl) |
| 509 | —NH$_2$ | 1-(1-cyclohexyl-4-pentenyl) |
| 510 | —NH(C(O)CH$_3$) | 1-(1-(4-tetrahydropyranyl)-3-carboxy-propyl) |

As used herein, unless otherwise noted, the term "halogen" shall mean chlorine, bromine, fluorine and iodine. Preferably, the halogen is fluoro or chloro. More preferably, the halogen is fluoro.

As used herein, unless otherwise noted, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{1-8}$alkyl" shall include straight and branched chains comprising one to eight carbon atoms.

As used herein, unless otherwise noted, the term "alkenyl" whether used alone or as part of a substituent group, shall include straight and branched chains containing at least one, preferably one to three, more preferably one to two, unsaturated double bonds. For example, alkenyl radicals include —CH=CH$_2$, 2-propenyl, 3-butenyl, 2-butenyl, 3,7-dimethyl-octa-2,6-dienyl, and the like. Similarly, the term "$C_{2-8}$alkenyl" shall include straight and branched alkenyl chains comprising two to eight carbon atoms.

As used herein, unless otherwise noted, the term "alkynyl" whether used alone or as part of a substituent group, shall include straight and branched chains containing at least one, preferably one to three, more preferably one to two, most preferably one, unsaturated triple bonds. For example, alkynyl radicals include —CCH (i.e. ethynyl), 2-propynyl, 3-butynyl, and the like. Similarly, the term "$C_{2-8}$alkynyl" shall include straight and branched alkynyl chains comprising two to eight carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "hydroxy substituted $C_{1-4}$alkyl" shall mean a straight or branched chain $C_{1-4}$alkyl, wherein the $C_{1-4}$alkyl is substituted with one or more, preferably one to three hydroxy groups, more preferably one to two hydroxy groups. Most preferably, the $C_{1-4}$alkyl group is substituted with one hydroxy group. Preferably, wherein the $C_{1-4}$alkyl group has a terminal carbon atom, the hydroxy group is bound at said terminal carbon atom.

As used herein, unless otherwise noted, "aryl" shall refer to fully conjugated aromatic ring structures such as phenyl, naphthyl, and the like.

As used herein, unless otherwise noted, the term "cycloalkyl" shall mean any stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norbornyl, adamantyl, spiropentane, 2,2,2-bicyclooctyl, and the like. Further, the term "$C_{5-7}$cycloalkyl" shall mean a cycloalkyl as herein defined containing 5 to 7 carbon atoms. Unless otherwise noted, "cycloalkyl" groups do not contain N, O or S heteroatoms.

As used herein, unless otherwise noted, the term "partially unsaturated carbocyclyl" shall mean any stable monocyclic, bicyclic, polycyclic, bridge or spiro-bound ring system containing at least one carbon atom which is not part of an unsaturated bond (i.e. a double or triple bond) or any bicyclic, polycyclic, bridged or spiro-bound, partially aromatic (e.g. benzo-fused) rings system. Suitable examples include, but are not limited to 1,2,3,4-tetrahydro-naphthyl, fluorenyl, 9,10-dihydroanthracenyl, indanyl, and the like. Unless otherwise noted, "partially unsaturated carbocyclyl" groups do not contain N, O or S heteroatoms.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, 5-tetrazolyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; or a 7-16 membered saturated, partially unsaturated or partially aromatic polycyclic or bridged ring system containing at least one heteroatom selected from the group consisting of O, N and S, optionally containing one or four additional heteroatoms independently selected from O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxolanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, 1-aza-bicyclo[2.2.2]octanyl, 3-quinuclidinyl, and the like.

As used herein, the notation "*" shall denote the presence of a stereogenic center.

When a particular group is "substituted" (e.g., cycloalkyl, aryl, heterocycloalkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example benzyl, tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetate, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-(C$_1$-C$_6$alkyl)-aminocarbonyl-(C$_1$-C$_6$alkyl)-" substituent refers to a group of the formula

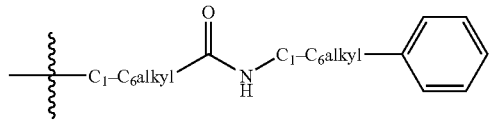

Unless otherwise noted, the position at which substituent groups on the compounds of formula (I) are bound to the 2-amino-quinoline core shall be denoted as follows:

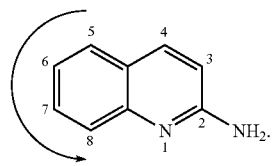

Similarly, unless otherwise noted, the position at which substituent groups on the compounds of formula (II) are bound to the 3,4-dihydro-2-amino-quinoline core shall be denoted as follows:

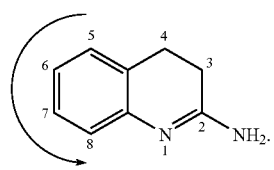

One skilled in the art will recognize that some substituent groups are bivalent (i.e. bound through two points of attachment), for example the substituent groups of A$^1$ and L$^1$ in the compounds of formula (I) and formula (II) as described herein. One skilled in the art will further recognize that the bivalency of these groups is defined by the two bond indicators—i.e. dashes—in the listing of said groups. For example, in the definition of A$^1$, the group —C$_{1-4}$-alkyl- is intended to mean an alkyl chain comprising one to four carbon atoms, wherein the chain is bivalent. Similarly, the A$^1$ group —CH$_2$-cyclopropyl- is intended that the -cyclopropyl- group is bivalent and therefore bound into the molecule such that one carbon atom is bound to the —CH$_2$— group of A$^1$ and at another carbon atom is bound to the rest of the molecule as defined herein.

Abbreviations used in the specification, particularly the Schemes and Examples, are as follows:

| | |
|---|---|
| Ac = | Acetyl (i.e. —C(O)—CH$_3$) |
| AD = | Alzheimer's Disease |
| APP = | Amyloid Precursor Protein |
| BACE = | Beta Amyloid Site Cleaving Enzyme |
| 9-BBN = | 9-Borobicyclo[3.3.1]nonane |
| DBU = | 1,8-Diazabicyclo[5.4.0]undec-7-ene |
| DCC = | N,N'-Dicyclohexylcarbodiimide |
| DCE = | Dichloroethane |
| DCM = | Dichloromethane |
| DIPEA or DIEA = | Diisopropylethylamine |
| DMAP = | 4-N,N-Dimethylaminopyridine |
| DMF = | N,N-Dimethylformamide |
| DMSO = | Dimethylsulfoxide |
| EDC or EDCl = | 1-(3-Dimethylaminopropyl)-3-ethylcarbodiimide hydrochoride |

-continued

| | |
|---|---|
| EtOAc = | Ethyl acetate |
| EtOH = | Ethanol |
| HBTU = | O-Benzotriazol-1-yl-N,N,N',N'-tetramethyluronium hexafluorophosphate |
| HEPES = | 4-(2-Hydroxyethyl)-1-Piperizine Ethane Sulfonic Acid |
| HOBT or 1-HOBt = | 1-Hydroxybenzotriazole |
| HPLC = | High Pressure Liquid Chromatography |
| LC/MS = | Liquid Chromatography/Mass Spectrometry |
| LDA = | Lithium Diisopropylamide |
| LHMDS = | Lithium hexamethylisilazide |
| MCI = | Mild Cognitive Impairment |
| MeOH = | Methanol |
| $Na_4OAc$ = | Sodium Acetate |
| NMR = | Nuclear Magnetic Resonance |
| OM99-2 = | 4-amino-4-{1-[2-carbamoyl-1-(4-{1-[3-carboxy-1-(1-carboxy-2-phenyl-ethylcarbamoyl)-propylcarbamoyl]-ethylcarbamoyl}-2-hydroxy-1-isobutyl-pentylcarbamoyl)-ethylcarbamoyl]-2-methyl-propylcarbamoyl}-butyric acid |
| Pd-C or Pd/C = | Palladium on Carbon Catalyst |
| t-BOC or Boc = | Tert-Butoxycarbonyl |
| t-Bu = | tert-butyl (—$C(CH_3)_3$) |
| TEA = | Triethylamine |
| TFA = | Trifluoroacetic Acid |
| THF = | Tetrahydrofuran |

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) wherein $L^1$ is —C(O)—$NR^C$— may be prepared according to the process outlined in Scheme 1.

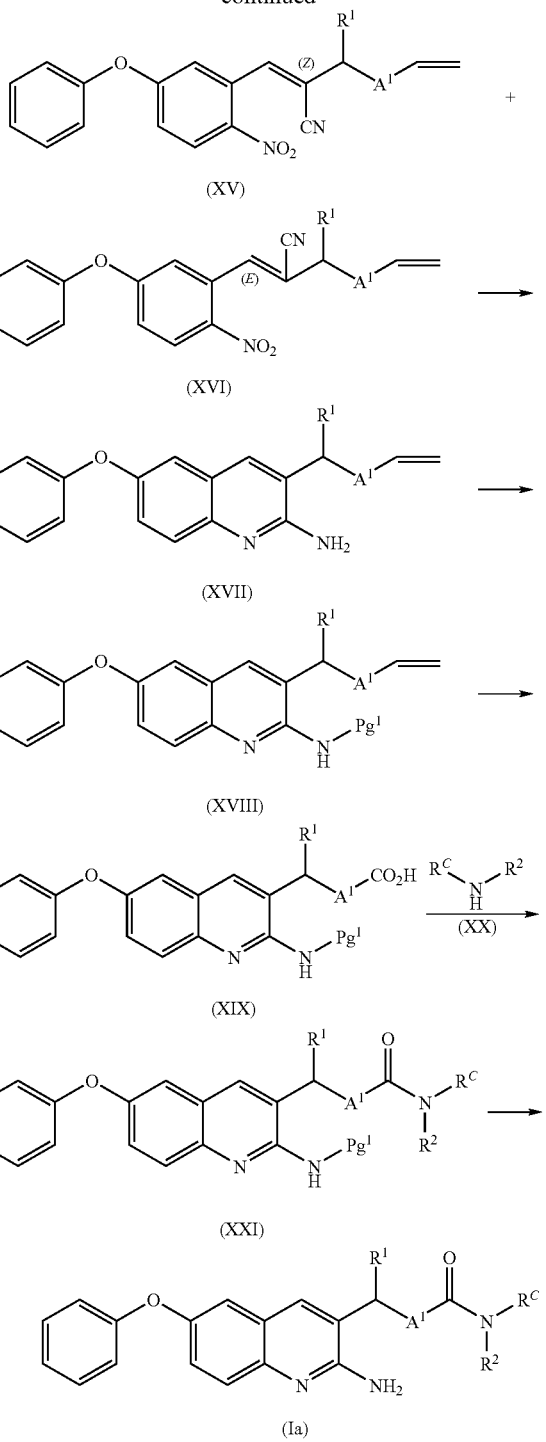

Accordingly, a suitably substituted compound of formula (X), a known compound or compound prepared by known methods is reacted with cyanomethyl-phosphonic acid diethyl ester, a known compound, in the presence of an organic amine such as $NH_4OAc$, piperidine, pyridine, and the like, in the presence of an acid such as acetic acid, formic acid, β-alanine, and the like, in an organic solvent such as toluene, ethanol, methanol, and the like, to yield the corresponding compound of formula (XI).

The compound of formula (XI) is reacted with a suitably substituted compound of formula (XII), a known compound or compound prepared by known methods, in the presence of a catalyst such as CuI, CuBr, and the like, in an organic solvent such as THF, diethyl ether, and the like, to yield the corresponding compound of formula (XIII).

The compound of formula (XIII) is reacted with a suitably substituted compound of formula (XIV), a known compound or compound prepared by known methods, in the presence of a base such as LHMDS, lithium diisopropylamide, sodium hydride, and the like, in an organic solvent such as THF, diethyl ether, and the like, at a temperature in the range of from about 60° C. to about 150° C., preferably at a temperature in the range of from about 75° C. to about 100° C., to yield a mixture of the corresponding compound of formula (XV) and (XVI), which are corresponding (Z) and (E) isomers.

The mixture of the compounds of formula (XV) and (XVI) is reacted with a reducing agent such as zinc, and the like, preferably zinc, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (XVII). Alternatively, the mixture of the compounds of formula (XV) and (XVI) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (XVII).

The compound of formula (XVII) is optionally reacted with a suitable protecting reagent, such as acetic anhydride, acetyl chloride, and the like, according to known methods, (i.e. in the presence of a base such as TEA, DMAP, and the like, in an organic solvent such as dichloromethane, chloroform, and the like) to yield the corresponding compound of formula (XVIII), wherein $Pg^1$ is the corresponding suitable nitrogen protecting group.

The compound of formula (XVIII) is reacted with an oxidizing agent such as potassium permanganate, osmium tetroxide, ruthenium tetroxide, sodium periodate, and the like, in a mixture of an organic solvent such as DCM, acetone, ethyl acetate, and the like, and water (as a co-solvent), to yield the corresponding compound of formula (XIX).

The compound of formula (XIX) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XXI).

The compound of formula (XXI) is de-protected according to known methods, for example by reacting with hydrazine, sodium hydroxide, and the like, in a protic solvent such as methanol or ethanol, at a temperature in the range of from about 60° C. to about 150° C., preferably at a temperature in the range of from about 75° C. to about 100° C., to yield the corresponding compound of formula (Ia).

Alternatively, compounds of formula (I) wherein $L^1$ is —C(O)—$NR^C$— may be prepared according to the process outlined in Scheme 2.

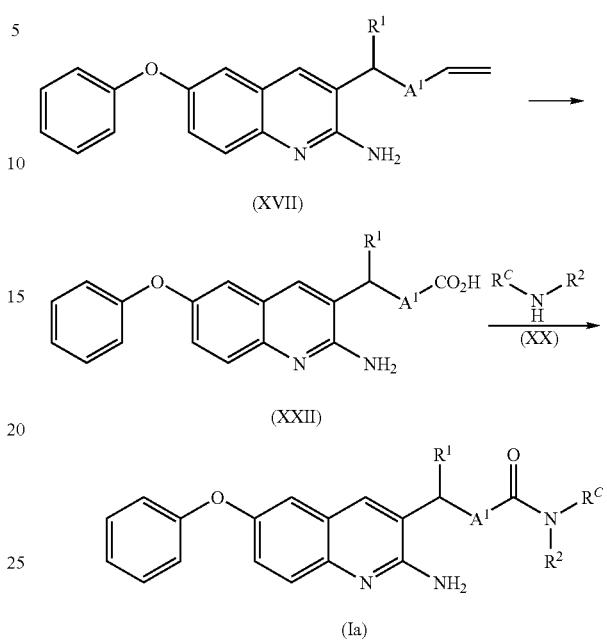

Accordingly, a compound of formula (XVII) is reacted with an oxidizing agent such as potassium permanganate, osmium tetroxide, ruthenium tetroxide, and sodium periodate and the like, in a mixture of an organic solvent such as DCM, acetone, ethyl acetate, and the like, and water (as a co-solvent), to yield the corresponding compound of formula (XXII).

The compound of formula (XXII) is reacted via a two step, one pot reaction, first with an alkyl chloroformate, such as iso-butyl chloroformate, and the like, in the presence of a base such as N-methylmorpholine, DIPEA, and the like, in an organic solvent such as dichloromethane, chloroform and the like, at a temperature less than about room temperature, preferably at a about 0° C.; and then with a suitably substituted compound of formula (XX), a known compound or compound prepared by known methods, yield the corresponding compound of formula (Ia).

Compounds of formula (I) wherein $L^1$ is —$NR^C$—C(O)— may be prepared according to the process outlined in Scheme 3 below.

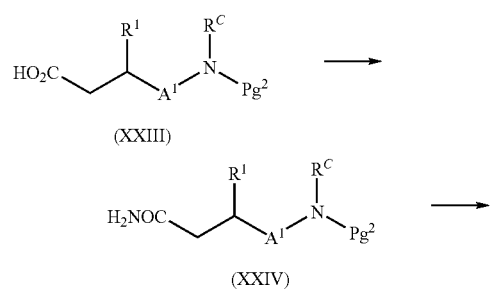

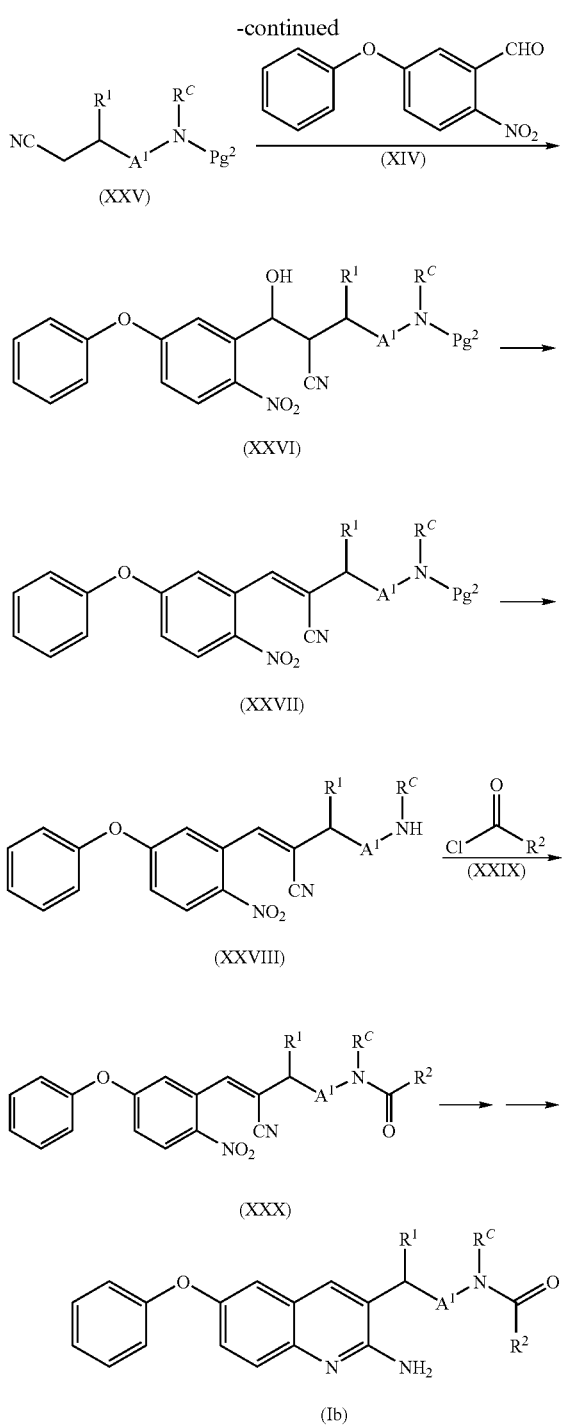

Alternatively, the compound of formula (XXIII) is reacted in a two step, one pot reaction, first by reacting with an activating agent, such as di-tert-butyl carbonate, iso-butyl-chloroformate, and the like, in the presence of a base, such as N-methylmorpholine, DIPEA, and the like, in the presence of a coupling reagent such as 1-HOBt, EDCl, DCC, and the like, in an organic solvent such as dichloromethane, DMF, and the like; then in the second step with ammonia in a mixture of a protic solvent such as MeOH, EtOH, $H_2O$, and the like, and an organic solvent, such as THF, and the like, to yield the corresponding compound of formula (XXIV).

The compound of formula (XXIV) is reacted with a dehydrating agent such as trifluoroacetic anhydride, triflic anhydride, tosyl chloride, and the like, in the presence of a base, such as triethyl amine, DIPEA, pyridine, and the like, in an organic solvent, such as THF, dichloromethane, and the like, with to yield the corresponding compound of formula (XXV).

The compound of formula (XXV) is reacted with a suitably substituted compound of formula (XIV), a known compound or compound prepared by known methods, in the presence of a base, such as LDA, LHMDS, NaH, and the like, in an organic solvent, such as THF, diethyl ether, and the like, to yield the corresponding compound of formula (XXVI).

The compound of formula (XXVI) is reacted with a sulfonylating agent, such as mesyl chloride, tosyl, chloride, and the like, in the presence of a base, such as triethylamine, DIPEA, DBU, and the like, in an organic solvent, such as dichloromethane, chloroform, DCE, and the like, at a temperature in the range of from about −20° to about 50° C., preferably at a temperature in the range of from about 0° C. to about 25° C., to yield the corresponding compound of formula (XXVII).

The compound of formula (XXVII), is deprotected according to known methods, for example where $Pg^2$ is Boc, the compound of formula (XXXVII) is reacted with an acid, such as trifluoroacetic acid, formic acid, and the like, in an organic solvent such as dichloromethane, chloroform, and the like, to yield the corresponding compound of formula (XXVIII).

The compound of formula (XXVIII) is reacted with a suitably substituted acid chloride of formula (XXIX) in the presence of a base, such as pyridine, triethylamine, DIPEA, or the like, in an organic solvent, such as dichloromethane, chloroform, dichloroethane, and the like, to yield the corresponding compound of formula (XXX).

The compound of formula (XXX) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (Ib). Alternatively, the compound of formula (XXX) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (Ib).

Accordingly, a suitably substituted compound of formula (XXIII), a known compound or compound prepared by known methods, is reacted with an ammonium salt, such as ammonium carbonate, ammonium chloride, ammonium hydroxide, and the like, in the presence of an activating agent, such as di-t-butyl dicarbonate, ethyl chloroformate, and the like, in the presence of a base, such a pyridine, triethylamine, and the like, in an organic solvent, such as dioxane, acetonitrile, THF, and the like, to yield the corresponding compound of formula (XXIV).

Compounds of formula (I) wherein $L^1$ is —$NR^C$— may be prepared according to the process outlined in Scheme 4 below.

Scheme 4
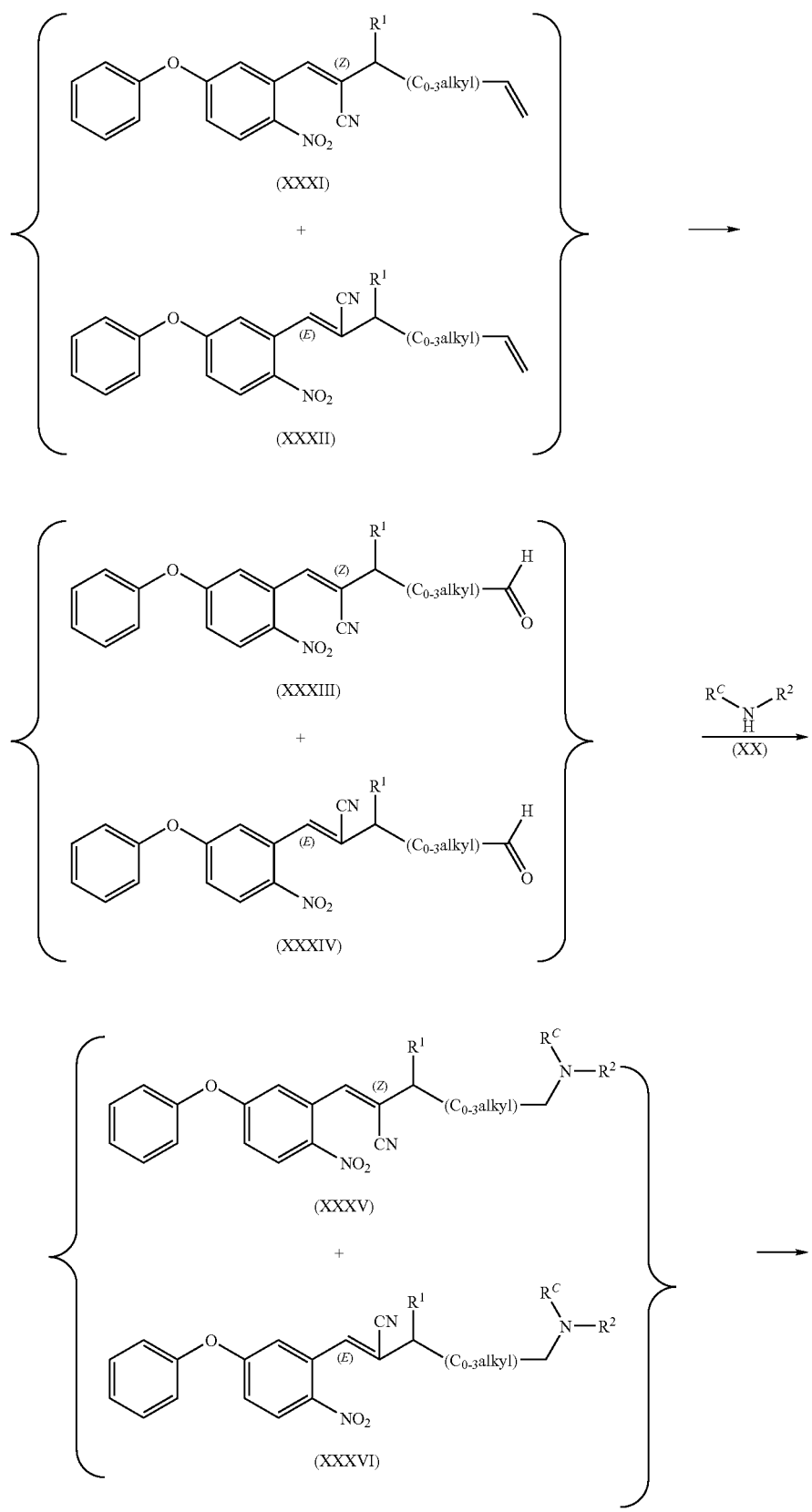

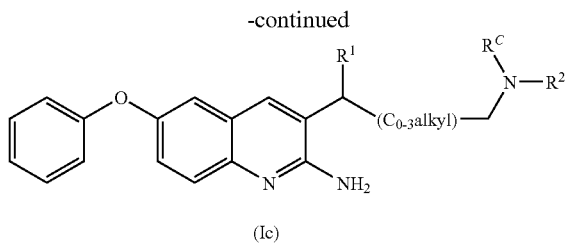

(Ic)

Accordingly, the mixture of suitably substituted compounds of formula (XXXI) and (XXXII), is reacted with an oxidizing agent such as potassium permanganate, osmium tetroxide, ruthenium tetroxide, sodium periodate and the like, in a mixture of an organic solvent such as DCM, acetone, ethyl acetate, and the like, and water (as a co-solvent), to yield a mixture of the corresponding compounds of formula (XXXIII) and (XXXIV).

The mixture of compounds (XXXIII) and (XXXIV) is reacted with a suitably substituted compound (XX), in the presence of a reducing agent, such as sodium triacetoxyborohydride, and the like, in an organic solvent, such as dichloromethane, dichloroethane, THF, and the like, or sodium borohydride in a protic solvent such as methanol or ethanol, or the like, to yield a mixture of the corresponding compounds of formula (XXXV) and (XXXVI).

Alternatively, the mixture of compounds (XXXIII) and (XXXIV) is reacted with a suitably substituted compound (XX), in the presence of sodium cyanoborohydride, in the presence of a catalytic amount of an acid, such as acetic acid, HCl, the like, in an organic solvent, such as methanol, acetonitrile, and the like, to yield a mixture of compounds (XXXV) and (XXXVI).

The mixture of compounds of formulas (XXXV) and (XXXVI) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (Ic). Alternatively, the mixture of compounds of formulas (XXXV) and (XXXVI) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (Ic).

Compounds of formula (I) wherein $A^1$ is —$CH_2$-cyclopropyl- may be prepared according to the process outlined in Scheme 5, below.

Scheme 5

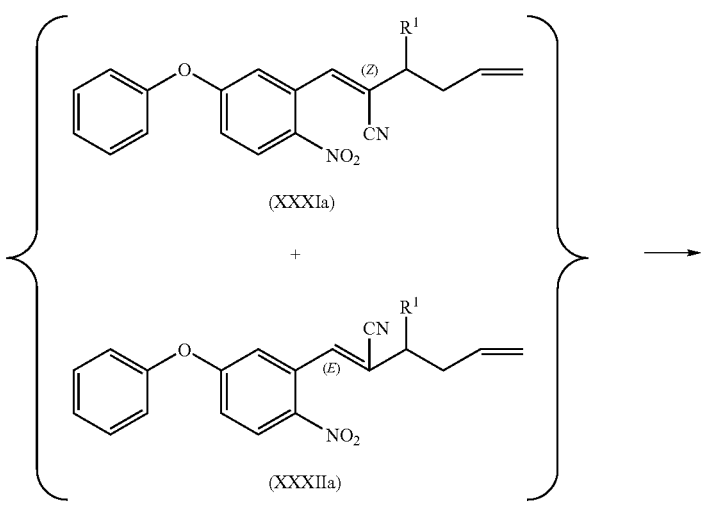

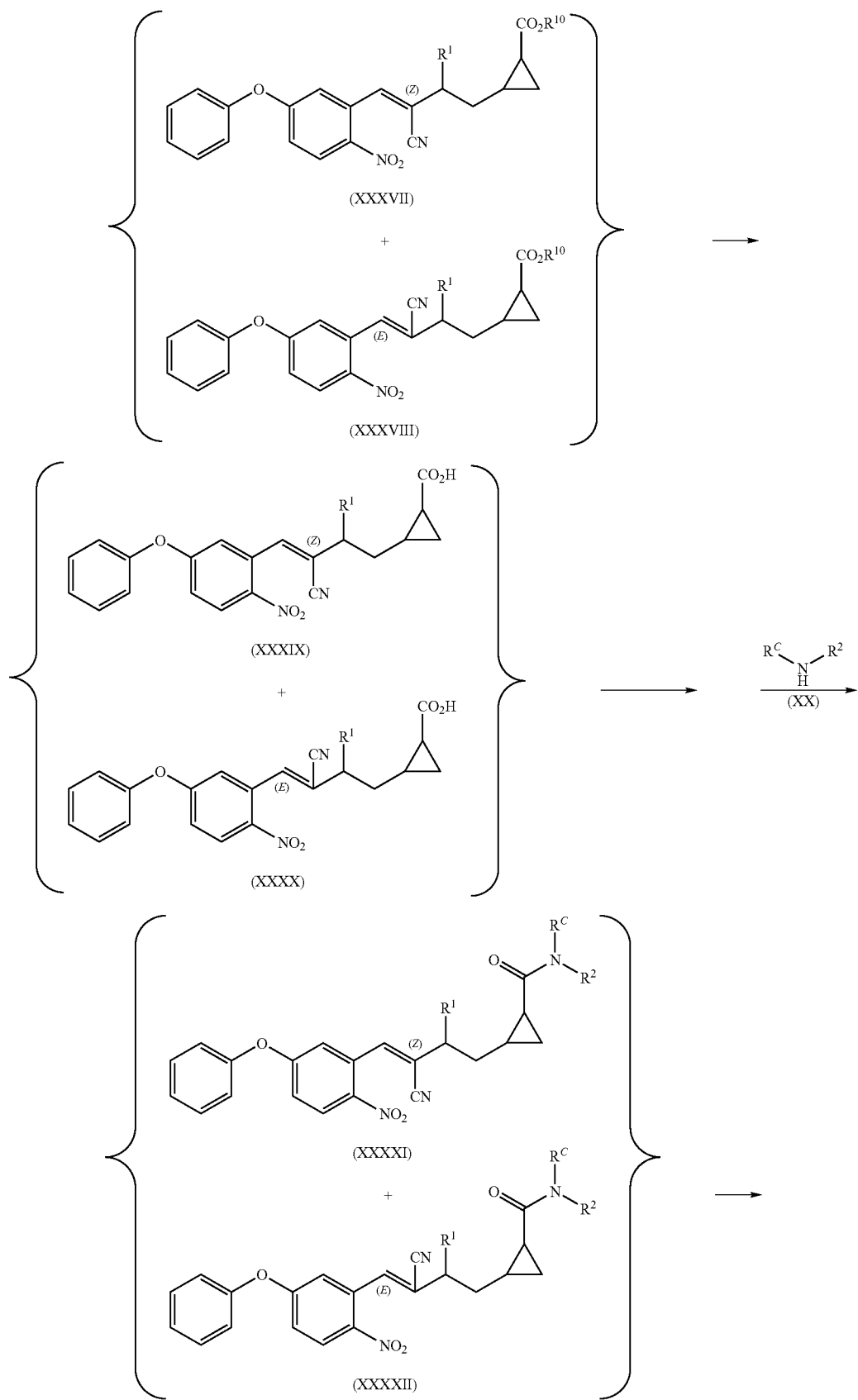

-continued

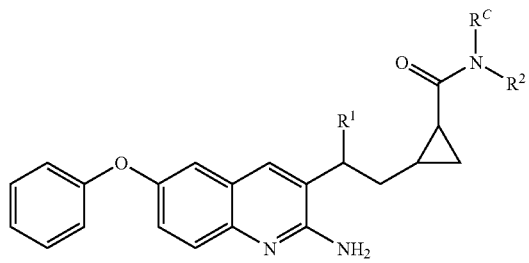

(Id)

Accordingly, a mixture of suitably substituted compounds of formula (XXXIa) and (XXXIIa) (compounds of formula (XXXI) and (XXXII) wherein the $C_{0-3}$alkyl is —$CH_2$—), is reacted with an cyclopropanating agent such as diazoethylacetate, and the like, in an organic solvent such as DCM, DCE, benzene, and the like, in the presence of a catalyst, such as dirhodium tetraacetate, dichlorotris(triphenylphosphine) ruthenium, copper acetonylacetate, and the like, to yield a mixture of the corresponding compounds of formulas (XXXVII) and (XXXVIII), wherein $R^{10}$ is $C_{1-4}$alkyl, preferably, methyl or ethyl.

Alternatively, a mixture of suitably substituted compounds of formula (XXXIa) and (XXXIIa), is reacted with a cyclopropanating agent such as diazoethylacetate, and the like, in an organic solvent such as DCM, DCE, benzene, and the like, at a temperature in the range of from about 40° C. to about 100° C., preferably at a temperature in the range of from about 65° C. to about 85° C., to yield a mixture of the corresponding compounds of formulas (XXXVII) and (XXXVIII), wherein $R^{10}$ is $C_{1-4}$alkyl, preferably, methyl or ethyl.

The mixture of compounds (XXXVII) and (XXXVIII) is reacted with a base, such as lithium hydroxide, sodium hydroxide, and the like, in water or in a protic solvent, such as methanol, ethanol, and the like, to yield a mixture of the corresponding compounds of formula (XXXIX) and (XXXX).

The mixture of compounds of formula (XXXIX) and (XXXX) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield a mixture of the corresponding compounds of formula (XXXXI) and (XXXXII).

The mixture of compounds of formulas (XXXXI) and (XXXXII) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (Id). Alternatively, the mixture of compounds of formulas (XXXXIII) and (XXXXIV) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (Id).

Compounds of formula (I) wherein $L^1$ is selected from the group consisting of —$N(R^C)$— and —C(O)—$N(R^C)$— and wherein $R^C$ and $R^2$ are taken together with the nitrogen atom to which they are bound to form a ring structure as defined herein, may be similarly prepared according to the procedures described in Scheme 1, Scheme 2 and Scheme 4 above by selecting a suitably substituted cyclic amine for the compound of formula (XX).

Compound of formula (I) wherein $A^1$ is —CH=CH— may be prepared according to the process outlined in Scheme 6, below.

Scheme 6
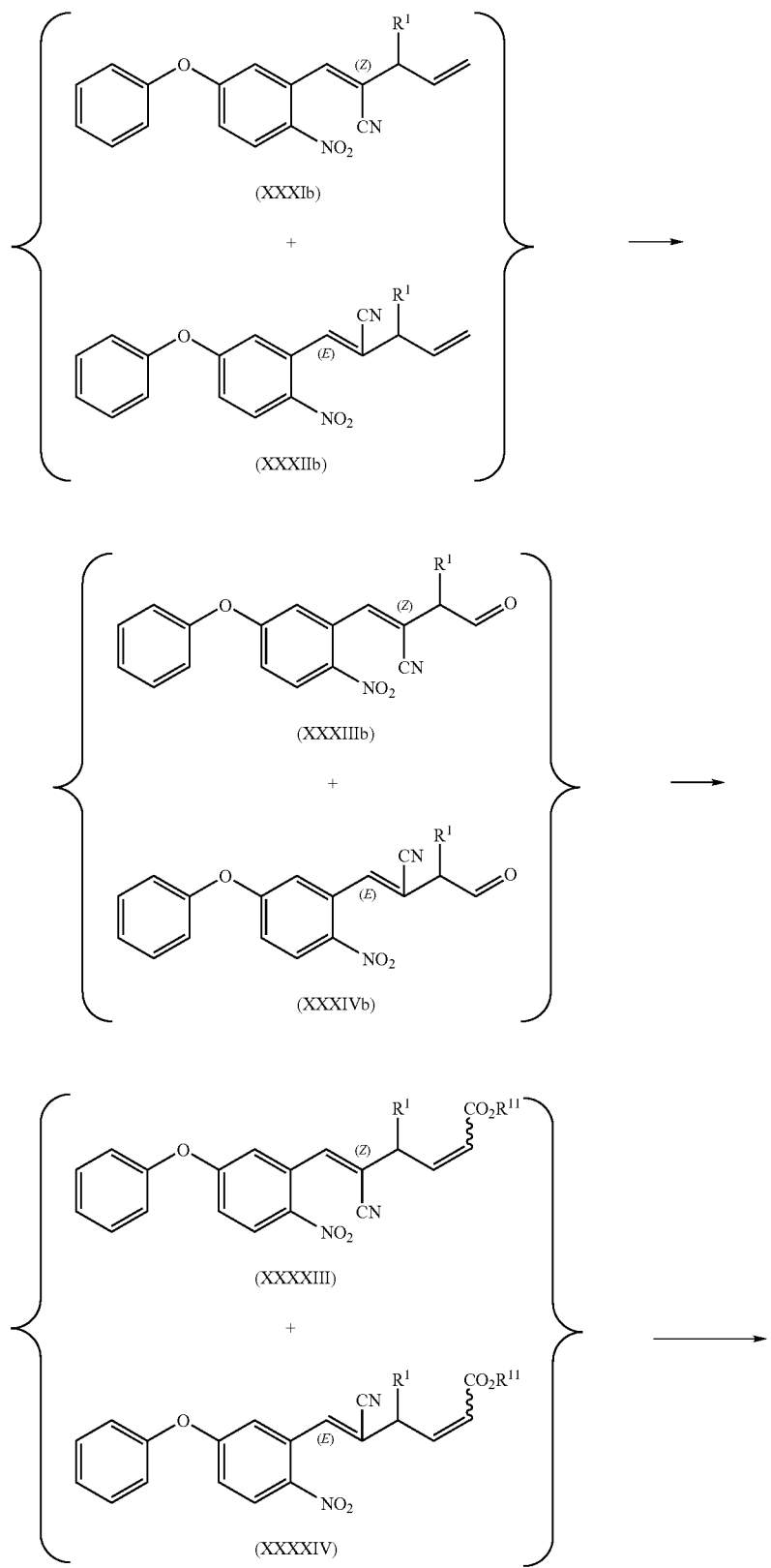

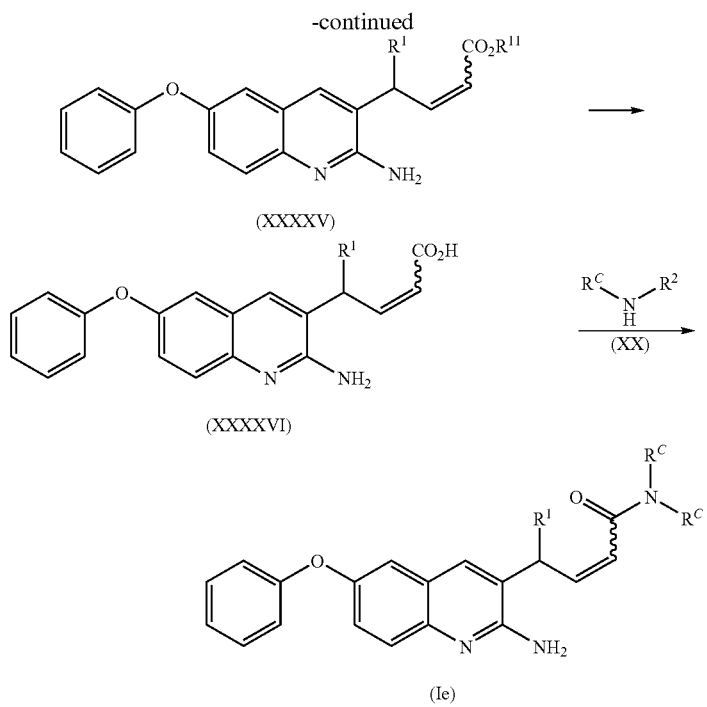

Accordingly, the mixture of suitably substituted compounds of formula (XXXIb) and (XXXIIb) (compounds of formula (XXXI) and (XXXII) wherein the $C_{0-3}$alkyl is —$C_0$alkyl-), is reacted with an oxidizing agent such as osmium tetroxide or sodium periodate, with a catalyst such as osmium trichloride, ruthenium trichloride, osmium tetroxide, and the like, in a mixture of an organic solvent such as DCM, acetone, butanol, and the like, and water (as a co-solvent), to yield a mixture of the corresponding compounds of formula (XXXIIIb) and (XXXIVb).

The mixture of compounds of formula (XXXIb) and (XXXIIb) is reacted with an alkyl dialkoxyphosphonoacetate, such as ethyl dimethoxyphosphonoacetate, in the presence of a base, such as LHMDS, LDA, NaH, and the like, in an organic solvent, such as THF, diethyl ether, glyme, and the like, to yield a mixture of the corresponding compounds of formula (XXXXIII) and (XXXXIV), wherein $R^{11}$ is $C_{1-4}$alkyl, preferably, methyl or ethyl.

The mixture of compounds of formulas (XXXXIII) and (XXXXIV) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (XXXXV). Alternatively, the mixture of compounds of formulas (XXXXIII) and (XXXXIV) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (XXXXV).

The compound of formula (XXXXV) is reacted with a base, such as lithium hydroxide, sodium hydroxide, in water or a protic solvent, such as methanol, ethanol, and the like, to yield a compound of formula (XXXXVI).

The compound of formula (XXXXVI) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (Ie).

Compounds of formula (II) wherein $L^1$ is —C(O)—$NR^C$— may be prepared by the process outlined in Scheme 7.

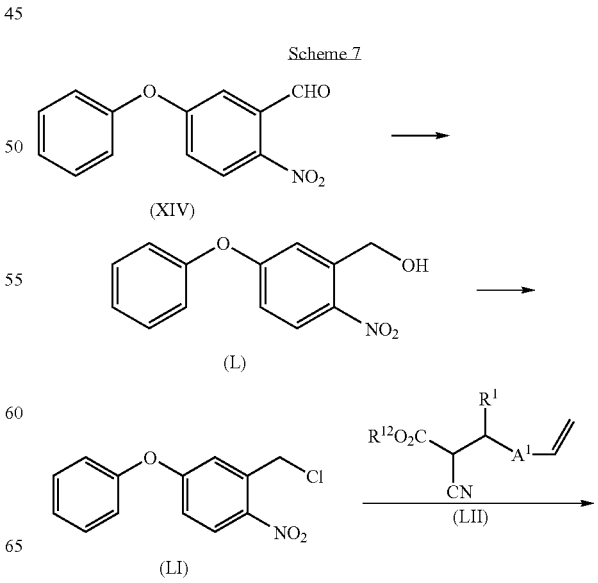

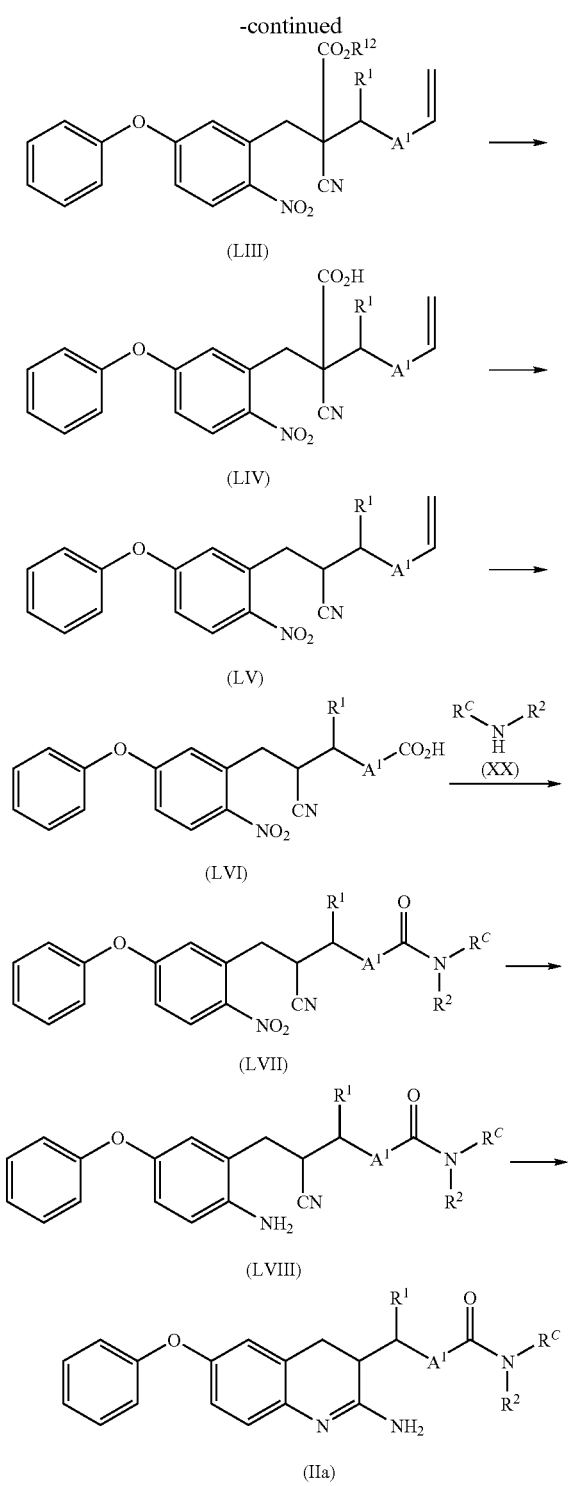

such as dichloromethane, chloroform, and the like, in the presence of a base, such as TEA, pyridine, DMAP, and the like, at a temperature in the range of from about 25° C. to about 75° C., preferably at a temperature in the range of from about 25° C. to about 40° C., to yield the corresponding compound of formula (LI).

The compound of formula (LII) is reacted with a base, such as sodium hydride, LDA, LHMDS, and the like, and with a suitably substituted compound of formula (LI), a known compound or a compound prepared by known methods, in an organic solvent such as THF, diethyl ether, DMF, glyme, and the like, to yield the corresponding compound of formula (LIII), wherein $R^{12}$ is $C_{1-4}$alkyl, preferably methyl or ethyl.

The compound of formula (LIII) is reacted with a base, such as lithium hydroxide, sodium hydroxide, and the like, in water or in a protic solvent, such as methanol, ethanol, and the like, to yield a compound of formula (LIV).

The compound of formula (LIV) is heated in an organic solvent, such as dimethylacetamide, xylenes, and the like, at a temperature in the range of from about 100° C. to about 250° C., preferably, at a temperature in the range of from about 150° C. to about 200° C., to yield the corresponding compound of formula (LV).

The compound of formula (LV) is reacted with an oxidizing agent such as potassium permanganate, osmium tetroxide, ruthenium tetroxide, sodium periodate, and the like, in a mixture of an organic solvent such as DCM, acetone, ethyl acetate, and the like, and water as the co-solvent, to yield the corresponding compound of formula (LVI).

The compound of formula (LVI) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (LVII).

The compound of formula (LVII) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (IIa). Alternatively, the compound of formula (LVII) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (LVIII).

The compound of formula (LVIII) is reacted with a Lewis acid, such as aluminum trichloride, stannic chloride, and the like, in an organic solvent, such as toluene, dichlorobenzene, and the like, at a temperature in the range of from about 50° C. to about 200° C., preferably at a temperature in the range of from about 80° C. to about 150° C., to yield the corresponding compound of formula (IIa).

Accordingly, a suitably substituted compound of formula (XIV) a known compound or compound prepared by known methods is reacted with a suitably selected reducing agent, such as sodium borohydride, lithium borohydride, and the like, in a protic solvent, such as methanol, ethanol, and the like, to yield the corresponding compound of formula (L).

The compound of formula (L) is reacted with a suitably selected chlorinating agent such as sulfonyl chloride, mesyl chloride, tosyl chloride, and the like, in an organic solvent, Compounds of formula (II) wherein $L^1$ is $-NR^C-C(O)-$ may be prepared by the process outlined in Scheme 8.

Scheme 8

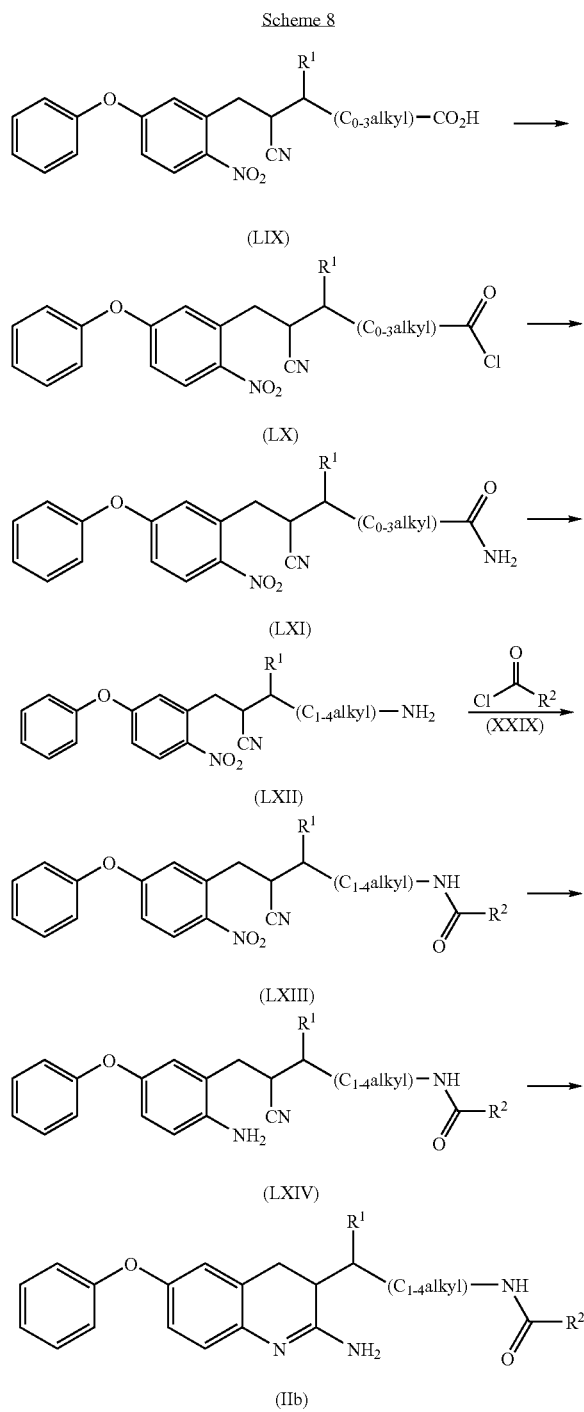

The compound of formula (LX) is reacted with ammonia in an organic solvent such as methanol, ethanol, THF, and the like, to yield the corresponding compound of formula (LXI).

The compound of formula (LXI) is reacted with a suitably selected reducing agent such as borane-tetrahydrofuran, lithium aluminum hydride, and the like, in an organic solvent such as diethyl ether, THF, toluene, glyme, and the like, in a temperature range of 25° C. to 100° C., preferably in the range of 25° C. to 70° C., optionally in a microwave, to yield the corresponding compound of formula (LXII).

The compound of formula (LXII) is reacted with a suitably substituted acid chloride of formula (XXIX), a known compound or compound prepared by known methods, in the presence of a base, such as pyridine, triethylamine, DIPEA, and the like, in an organic solvent, such as dichloromethane, chloroform, dichloroethane, and the like, to yield the corresponding compound of formula (LXIII).

The compound of formula (LXIII) is reacted with a suitably selected reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (LXIV). Alternatively, the compound of formula (LXIII) is reacted with a suitably selected reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (LXIV).

The compound of formula (LXIV) is reacted with a Lewis acid, such as aluminum trichloride, stannic chloride, and the like, in an organic solvent, such as toluene, dichlorobenzene, and the like, at a temperature in the range of from about 50° C. to about 200° C., preferably at a temperature in the range of from about 80° C. to about 150° C., to yield the corresponding compound of formula (IIb).

Compounds of formula (II) wherein $L^1$ is —$NR^C$— may be prepared by the process outlined in Scheme 9.

Scheme 9

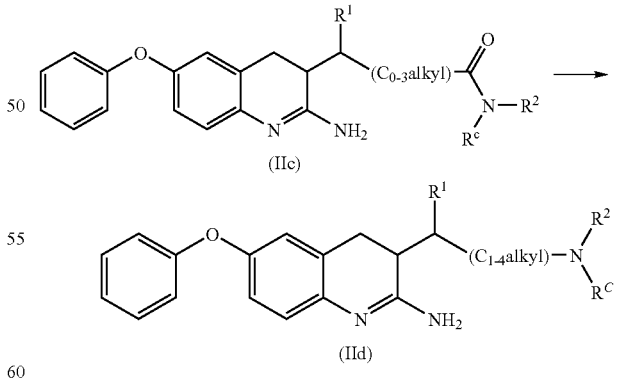

Accordingly, a suitably substituted compound of formula (LIX) is reacted with a chlorinating agent, such as oxalyl chloride, in an organic solvent, such as dichloromethane, chloroform, benzene, and the like, optionally with DMF, or sulfonyl chloride, and the like, either neat or in an organic solvent, such as dichloromethane, chloroform, and the like, at a temperature in the range of from about 0° C. to about 80° C., preferably at a temperature in the range of from about 0° C. to about 25° C., to yield the corresponding compound of formula (LX).

Accordingly, a suitably substituted compound of formula (IIc), prepared for example, as in Scheme 7 above, is reacted with a suitably selected reducing agent such as borane-tetrahydrofuran, lithium aluminum hydride, and the like, in an organic solvent such as diethyl ether, THF, toluene, or glyme, and the like, in a temperature range of 25° C. to 10° C., preferably in the range of 25° C. to 70° C., optionally in a microwave, to yield the corresponding compound of formula (IId).

The present invention further comprises pharmaceutical compositions containing one or more compounds of formula (I) and/or compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-1000 mg/kg/day, preferably, at a dosage of from about 0.5 to about 500 mg/kg/day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by BACE described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by BACE is required.

The daily dosage of the products may be varied over a wide range from 0.01 to 10,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1-1000 mg/kg/day, preferably, at a dosage of from about 0.5 to about 500 mg/kg/day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

[1-Cyano-2-(tetrahydro-pyran-4-yl)-vinyl]-phosphonic acid diethyl ester

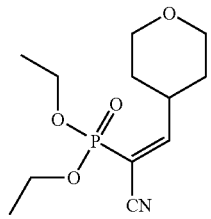

Tetrahydropyran carboxaldehyde (10 g, 87.6 mmol), diethyl cyanoacetophosphonate (16.3 g, 92 mmol), acetic acid (3 mL, 50 mmol) and ammonium acetate (3 g, 38.9 mmol) were combined in toluene (60 mL), and the reaction mixture was stirred overnight at room temperature. The reaction mixture was heated at 100° C. for two hours and then filtered through MgSO$_4$. The filtrate was evaporated in vacuo to yield a crude oil which was purified via flash silica column (50% EtOAc/heptane) to yield the title compound as an oil.

Example 2

[1-Cyano-2-(tetrahydro-pyran-4-yl)-hex-5-enyl]-phosphonic acid diethyl ester

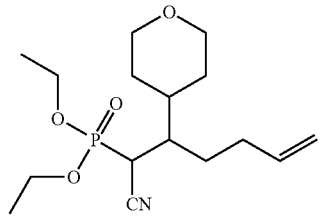

In a reaction flask, Mg (5.7 g) was placed in THF (50 mL) with an iodine chip. The reaction mixture was stirred vigorously, as 4-bromobutene (25 mL) was added. The reaction mixture was then heated slightly. After consumption of the Mg metal, the reaction mixture was cannulated into a flask containing a mixture of [1-cyano-2-(tetrahydro-pyran-4-yl)-vinyl]-phosphonic acid diethyl ester (21.78 g, 79.7 mmol) and CuI (0.3 g) in THF (30 mL). The reaction mixture was

Example 3

5-Cyano-5-(diethoxy-phosphoryl)-4-(tetrahydro-pyran-4-yl)-pentanoic acid

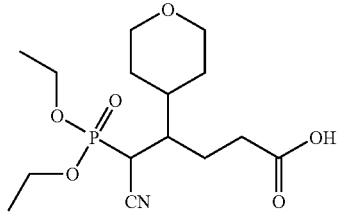

In a flask, [1-cyano-2-(tetrahydro-pyran-4-yl)-hex-5-enyl]-phosphonic acid diethyl ester (7.18 g, 21.6 mmol), dichloromethane (245 mL), acetic acid (70 mL), tetrabutylammonium bromide (490 mg), and water (210 mL) were combined and stirred at room temperature. KMnO₄ (15.35 g, 97.2 mmol) was then added portionwise over the next 3 hours, and the reaction mixture was stirred overnight at room temperature. Solid NaHSO₃ was added carefully until the reaction mixture became clear. The reaction mixture layers were separated, and the solvent was removed in vacuo to yield the title compound as a residue.

Example 4

5-Cyano-6-(2-nitro-5-phenoxy-phenyl)-4-(tetrahydro-pyran-4-yl)-hex-5-enoic acid

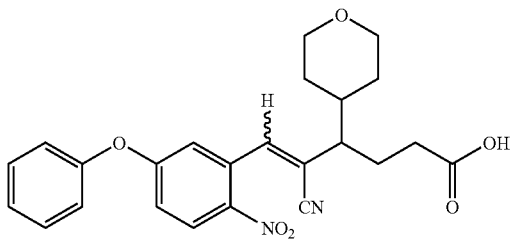

To a solution of 5-cyano-5-(diethoxy-phosphoryl)-4-(tetrahydro-pyran-4-yl)-pentanoic acid (2.68 g, 7.7 mmol) in THF (300 mL), sodium hydride (60%, 1.24 g) was added portionwise at room temperature. 2-Nitro-5-phenoxy-benzaldehyde (1.9 g, 7.7 mmol) was then added, and the reaction mixture was stirred at room temperature overnight. Ethyl acetate was added to the reaction mixture, and the resulting solution washed with saturated aqueous NH₄Cl solution. The organic phase was separated, dried with MgSO₄, and filtered. The filtrate was evaporated in vacuo to yield an oil which was triturated with heptane to yield the title compound as a solid.

Example 5

5-Cyano-6-(2-nitro-5-phenoxy-phenyl)-4-(tetrahydro-pyran-4-yl)-hex-5-enoic acid cyclohexyl-methyl-amide

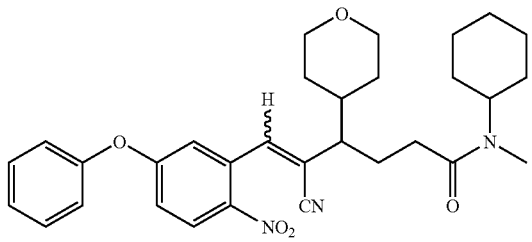

A solution of 5-cyano-6-(2-nitro-5-phenoxy-phenyl)-4-(tetrahydro-pyran-4-yl)-hex-5-enoic acid (0.87 g, 2 mmol), N-methylcyclohexylamine (0.26 mL, 2 mmol), HBTU (1.13 g, 3 mmol), DIPEA (1.2 mL, 7 mmol) in DMF (20 mL) was stirred at room temperature overnight. Ethyl acetate was added to the reaction mixture. The solution washed with saturated aqueous NaHCO₃ solution. The organic phase was separated and dried with MgSO₄, and filtered. The solvent was removed in vacuo to yield the title compound as an oil.

Example 6

4-(2-Amino-6-phenoxy-quinolin-3-yl)-N-cyclohexyl-N-methyl-4-(tetrahydro-pyran-4-yl)-butyramide

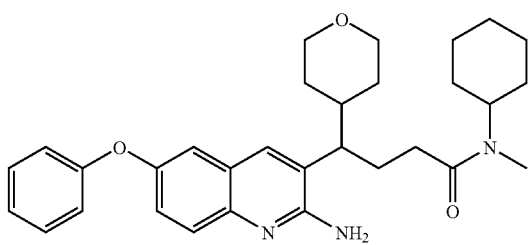

A solution of 5-cyano-6-(2-nitro-5-phenoxy-phenyl)-4-(tetrahydro-pyran-4-yl)-hex-5-enoic acid cyclohexyl-methyl-amide (0.37 g, 0.697 mmol) in methanol was divided evenly into two microwave tubes containing Zn (0.9 g, 13.8 mmol) and NH₄Cl (0.1 g, 1.87 mmol). The reaction mixture was subjected to μW at 95° C. for 900 sec. The reaction mixture was filtered through Celite®, and the filtrate was evaporated in vacuo to yield a crude product which was purified on a silica gel column (10% MeOH/dichloromethane) to yield the title compound as a residue.

$^1$H NMR (300 MHz, CDCl$_3$) δ7.7 (d, 1H), 7.6 (s, 1H), 7.3-7.42 (m, 3H), 7.0-7.1 (m, 4H), 5.05 (bs, 2H), 4.4 (m, 1H), 4.0 (m, 1H), 3.85 (m, 1H), 3.2-3.4 (m, 2H), 3.6-3.8 (m, 4H), 2.2-2.4 (m, 2H), 2.0-2.2 (m, 1H), 1.0-2.0 (m, 16H)

HPLC R$_t$=4.94

MS m/z (ES) MH+=501.9.

Example 7

4-(2-Amino-6-phenoxy-quinolin-3-yl)-N-(3,3-dimethyl-butyl)-N-(1-methyl-1H-imidazol-2-ylmethyl-4-(tetrahydropyran-4-yl)-butyramide

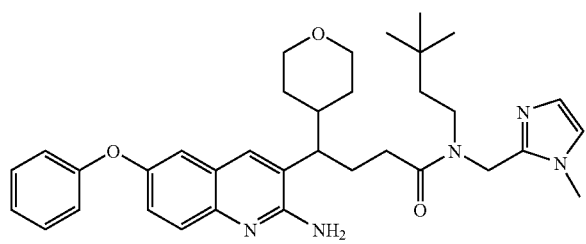

Step A: [1-Cyano-2-(tetrahydropyran-4-yl)-vinyl]-phosphonic acid diethyl ester To a stirred solution of diethyl cyanomethylphosphonate (50.0 g, 282 mmol), ammonium acetate (9.0 g, 117 mmol), acetic acid (9 ml) in toluene (200 mL), tetrahydropyran-4-carbaldehyde (32.2 g, 282 mmol) were added. The reaction mixture was stirred at room temperature for two hours and then heated at reflux for 1.5 hours. After cooling down, the reaction mixture washed with saturated sodium bicarbonate solution three times, brine one time and then dried over magnesium sulfate. The reaction mixture was filtered and concentrated to yield a residue. The residue was purified by Kugelrohr distillation to yield [1-cyano-2-(tetrahydropyran-4-yl)-vinyl]-phosphonic acid diethyl ester as a colorless oil.
MH$^+$=274.03

Step B: [1-Cyano-2-(tetrahydro-pyran-4-yl)-hex-5-enyl]-phosphonic acid diethyl ester To a stirred solution of the oil isolated in Step A (51.26 g, 188 mmol) in THF (200 mL) at −30° C., 3-butenylmagnesium bromide in THF (0.5 M, 394 mL, 197 mmol) was added slowly. The reaction mixture was stirred at room temperature overnight. Aqueous saturated ammonium chloride solution (300 mL) was then added. The reaction mixture was stirred 30 min at room temperature and then was extracted with ethyl acetate (400 mL) once. The organic solution washed with saturated ammonium chloride solution three times, with brine one time and then was dried over magnesium sulfate. The reaction mixture was then filtered and concentrated to yield a residue. The residue was purified by Kugelrohr distillation to yield [1-cyano-2-(tetrahydro-pyran-4-yl)-hex-5-enyl]-phosphonic acid diethyl ester as a colorless oil.
MH$^+$=330.14.

Step C: 6-Phenoxy-3-[1-(tetrahydro-pyran-4-yl)-pent-4-enyl]-quinolin-2-ylamine To the oil isolated in Step B (23.28 g, 70.7 mmol) in THF (100 mL) at −78° C., LHDMS (1.0 M, 84.8 mL, 84.8 mmol) was added slowly. The reaction mixture was then stirred at room temperature for 1 hour. A solution of 2-nitro-5-phenoxybenzaldehyde (20.63 g, 75.5 mmol) in THF (100 mL) was added. The reaction mixture was stirred at room temperature overnight. Saturated aqueous ammonium chloride (200 mL) was added. The reaction mixture was extracted with ethyl acetate three times. The combined organic extracts were washed with brine and dried over magnesium sulfate. The reaction mixture was filtered and concentrated to yield a colorless oil which was a mixture of cis-[2-(2-nitro-5-phenoxy-benzylidene)-3-(tetrahydro-pyran-4-yl)-hept-6-enenitrile] and trans-[2-(2-nitro-5-phenoxy-benzylidene)-3-(tetrahydro-pyran-4-yl)-hept-6-enenitrile].

Step D: 6-Phenoxy-3-[1-(tetrahydro-pyran-4-yl)-pent-4-enyl]-quinolin-2-ylamine The oil (product mixture) was dissolved in methanol (200 mL). Zinc (97 g, 1.48 mol) and ammonium chloride (11.34 g, 212 mmol) were added to the reaction mixture which was then refluxed for two days. After cooling to room temperature, aqueous ammonium hydroxide solution (20 mL) was added. The reaction mixture was filtered and concentrated to yield a residue. The residue was dissolved in ethyl acetate (300 mL). The resulting solution washed with saturated aqueous bicarbonate one time. The aqueous phase was separated and extracted with ethyl acetate three times. The combined organic phases were extracted with brine and dried over magnesium sulfate. The resulting solution was filtered and concentrated to yield a residue. The residue was purified on a silica gel column eluted with a mixture of acetone:methylene:chloride (2:98) to yield 6-phenoxy-3-[1-(tetrahydro-pyran-4-yl)-pent-4-enyl]-quinolin-2-ylamine as a lightly colored solid.
MH$^+$=389.16.

Step E: N-{6-Phenoxy-3-[1-(tetrahydro-pyran-4-yl)-pent-4-enyl]-quinolin-2-yl}-acetamide To a stirred solution of the solid isolated in Step D (5.08 g, 17.6 mmol) in acetic anhydride (20 mL), sulfuric acid (1 drop) was added. The reaction mixture was stirred at room temperature for four hours. The reaction mixture was then concentrated to yield a residue. The residue was dissolved in ethyl acetate (300 mL). The resulting solution was extracted with sodium hydroxide (1.0 N) solution twice, hydrochloric acid (1.0 N) once, and brine once, and then was dried over magnesium sulfate. The solution was filtered and concentrated to yield N-{6-phenoxy-3-[1-(tetrahydro-pyran-4-yl)-pent-4-enyl]-quinolin-2-yl}-acetamide as a yellow solid.
MH$^+$=431.16

Step F: 4-(2-Acetylamino-6-phenoxy-quinolin-3-yl)-4-(tetrahydro-pyran-4-yl)-butyric acid To a stirred solution of the solid isolated in Step E (6.49 g, 15.1 mmol), tetrabutylammonium bromide (0.078 g, 0.24 mmol), acetic acid (16 mL) in a mixture of benzene (140 mL) and water (140 mL) at 0° C., potassium permanganate (8.34 g, 52.8 mmol) was added slowly. The reaction mixture was then stirred at room temperature for two hours. Sodium bisulfite was added portion wise slowly into the reaction mixture until the color disappeared. The reaction mixture was made basic by adding sodium hydroxide solution (1.0 N). The resulting solution was extracted with diethyl ether twice. The aqueous phase was made acidic (pH 2) by adding hydrochloric acid (3 N). The resulting solution was extracted with chloroform three times. The combined chloroform extracts were washed with brine and dried over magnesium sulfate. The solution was filtered and concentrated to yield 4-(2-acetylamino-6-phenoxy-quinolin-3-yl)-4-(tetrahydro-pyran-4-yl)-butyric acid as a yellow solid.
MH$^+$=449.11

Step G: (3,3-Dimethyl-butyl)-(1-methyl-1H-imidazol-2-ylmethyl)-amine

To a stirred solution of 3,3-dimethylbutylamine (2.81 g, 27.8 mmol) and 1-methyl-1H-imidazole-2-carbaldehyde (3.21 g, 29.1 mmol) in methanol (30 mL) at room temperature, sodium borohydride (1.05 g, 27.8 mmol) was added. The reaction mixture was then stirred at room temperature for 1 hour. The reaction mixture was concentrated, and hydrochloric acid (6 N, 5 mL) was then added. The resulting solution washed with diethyl ether once. The aqueous phase was made basic by adding sodium hydroxide solution (3 N). The resulting solution was extracted with chloroform three times. The combined chloroform extracts were washed with brine and dried over magnesium sulfate. The solution was filtered and concentrated to yield (3,3-dimethyl-butyl)-(1-methyl-1H-imidazol-2-ylmethyl)-amine as a colorless oil.

$MH^+$=196.23

Step H: 4-(2-Amino-6-phenoxy-quinolin-3-yl)-N-(3,3-dimethyl-butyl)-N-(1-methyl-1H-imidazol-2-ylmethyl-4-(tetrahydropyran-4-yl)-butyramide To a stirred solution of the solid isolated in Step F (0.427 g, 0.95 mmol), the oil isolated in Step G (0.372 g, 1.9 mmol), and N,N-diisopropylethylamine (0.34 ml, 1.9 mmol) in DMF (20 mL), HBTU (0.541 g, 1.43 mmol) were added. The reaction mixture was then stirred at room temperature overnight. Hydrazine (2.0 mL) was added and the reaction mixture solution was stirred at 75° C. for 1 hour. After cooling, water and methanol were added to the reaction mixture which was purified on the Gilson HPLC to yield residue, a TFA salt. The residue was dissolved in ethyl acetate (100 mL). The resulting solution was extracted with saturated aqueous sodium bicarbonate solution three times and dried over magnesium sulfate. The resulting solution was filtered and concentrated to yield a residue. The residue was dissolved in hydrochloric acid (2.0 N, 10 mL) and lyophilized to yield the title compound, 4-(2-Amino-6-phenoxy-quinolin-3-yl)-N-(3,3-dimethyl-butyl)-N-(1-methyl-1H-imidazol-2-ylmethyl-4-(tetrahydropyran-4-yl)-butyramide, as its corresponding HCl salt, as a lightly colored solid.

$MH^+$=584.46

$^1$H NMR (300 MHz, DMSO), 68.60 (s, 2H), 7.76 (d, J=9 Hz, 1H), 7.56 (s, 1H), 7.42-7.54 (m, 4H), 7.22 (m, 1H), 7.08 (d, J=7 Hz, 2H), 5.30 (br s, 2H), 4.70 (s, 2H), 3.74 (br s, 4H), 3.15 (br s, 5H), 2.20 (m, 3H), 1.80 (m, 3H), 1.10-1.35 (m, 6H), 0.64 (s, 9H).

Example 8

4-(2-amino-6-phenoxy-quinolin-3-yl)-4S-cyclohexyl-N-(3,3-dimethyl-butyl)-N-(1-methyl-1H-imidazol-2-ylmethyl)-butyramide

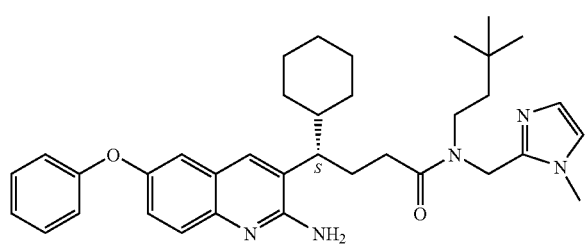

Step A: 4-Benzyl-3-(2-cyclohexyl-acetyl)-oxazolidin-2-one

Thionyl chloride (20.0 mL) was added dropwise to cyclohexyl acetic acid (10.0 g, 70 mmol). After cessation of gas evolution, the reaction mixture was heated to reflux overnight. The reaction mixture was then concentrated in vacuo to yield cyclohexyl acetyl chloride. To a solution of (S)-(–)-4-benzyl-2-oxazolidinone (11.6 g, 65 mmol) in THF (130 mL) at –60° C. was added 1.6 M n-butyl lithium (42 mL, 67 mmol), dropwise, and the reaction mixture was stirred for 0.5 h. To the resulting solution was then added the cyclohexylacetyl chloride, and the resulting mixture was stirred at 0° C. for 2 h. The reaction was quenched with aqueous saturated $NaHCO_3$ solution and extracted with ethyl acetate. The organic layer was dried ($MgSO_4$) and concentrated until a slurry was formed. The slurry was filtered and washed with cold diethyl ether. The filtrate was re-concentrated to yield a solid. The combined solid, 4-benzyl-3-(2-cyclohexyl-acetyl)-oxazolidin-2-one, was dried in vacuo.

$MH^+$ 302

Step B: (4-Benzyl-3-(2-cyclohexyl-pent-4-enoyl)-oxazolidin-2-one)

To a solution of 4-benzyl-3-(2-cyclohexyl-acetyl)-oxazolidin-2-one (16.0 g, 53 mmol) in anhydrous tetrahydrofuran at –78° C. was added a 1.0 M solution of sodium bis(trimethylsilyl)-amide (79.0 mL, 79 mmol), and the reaction mixture was stirred for 1 h. To the reaction mixture was then added allyl bromide (18.4 mL, 213 mmol), and the temperature was raised to –45° C. The reaction mixture was stirred at this temperature for 3 h. The reaction was quenched with aqueous saturated $NH_4Cl$ solution, and the resulting mixture was warmed to room temperature. The reaction mixture was extracted with ethyl acetate, and the combined extracts were washed with brine. The organic layers were dried ($MgSO_4$) and concentrated in vacuo to yield a residue that was purified by silica gel column chromatography (5:1 hexanes:ethyl acetate) to yield (4-benzyl-3-(2-cyclohexyl-pent-4-enoyl)-oxazolidin-2-one) as a thick liquid that became a solid upon storage.

$MH^+$ 342.20

Step C: 2-Cyclohexyl-pent-4-enethioic acid-(S)-ethyl ester

To a solution of ethanethiol (8.5 mL, 115 mmol) in anhydrous tetrahydrofuran (200 mL) at –78° C. was added n-butyl lithium (1.6 M in hexanes, 53.3 mL, 85 mmol). The resulting white suspension was stirred at 0° C. for 1 h. The reaction mixture was then treated with a tetrahydrofuran solution (100 mL) of 4-benzyl-3-(2-cyclohexyl-pent-4-enoyl)-oxazolidin-2-one (11.5 g, 34 mmol) dropwise. The ice-bath was removed, and the reaction mixture was stirred at room temperature for 1.5 h. Aqueous 1N NaOH (50 mL) solution was added. The organic layer was separated, washed twice with 1 N NaOH solution. The organic layer was dried ($MgSO_4$) and concentrated to yield a residue that was purified by silica gel column chromatography to yield 2-cyclohexyl-pent-4-enethioic acid-(S)-ethyl ester.

$MH^+$ 227

Step D: (S)-2-Cyclohexyl-pent-4-en-ol

To an ice cold suspension of lithium aluminum hydride (2.7 g, 70.5 mmol) in tetrahydrofuran (80 mL) was added, dropwise, a solution of 2-cyclohexyl-pent-4-enethioic acid-(S)-ethyl ester (4.0 g, 17.6 mmol) in tetrahydrofuran (40 mL). The ice-bath was removed, and the reaction mixture was stirred for 5 h at room temperature. The reaction mixture was then cooled to 0° C., and the reaction was quenched by dropwise addition of $H_2O$ (2 mL) and then 15% aqueous NaOH (2 mL) followed by another 6 mL of $H_2O$. After stirring for 1 h, the reaction mixture was treated with solid $Na_2SO_4$ (500 mg) and diethyl ether (50 mL). The resulting suspension was filtered and the organic layer was concentrated in vacuo to yield a residue that was purified by Kugelrohr distillation (0.20 mm Hg, 90-100° C.) to yield (S)-2-cyclohexyl-pent-4-en-ol.

$MH^+$ 169

Step E: (R)-3-Cyclohexyl-hex-5-enenitrile

To an ice cold solution of (S)-2-cyclohexyl-pent-4-en-ol (3.4 g, 20 mmol) in pyridine (50 mL) was added p-toluenesulfonyl chloride (8.4 g, 44 mmol) and dimethylaminopyridine (5.4 g, 44 mmol). The reaction mixture was stirred for 24 h at room temperature. To the reaction mixture was then added water (20 mL), and the resulting mixture was extracted with ethyl acetate (3×20 mL). The organic layer washed with saturated aqueous $NaHCO_3$ solution and dried over $MgSO_4$. The solvent was removed in vacuo, and the resulting crude material was carried to the next step without further purification.

To the crude product, (S)-toluene-4-sulfonic acid 2-cyclohexyl-pent-4-enyl ester, in DMSO (40 mL) was added NaCN, and the resulting mixture was heated at 90° C. for 1.5 h. The reaction mixture was cooled to room temperature and treated with $H_2O$ (20 mL). The reaction mixture was then extracted with diethylether (3×25 mL), dried ($MgSO_4$) and concentrated in vacuo to yield a residue which was purified by Kugelrohr distillation (0.19 mm Hg, 80-90° C.) to yield (R)-3-cyclohexyl-hex-5-enenitrile.

$MH^+$ 178.2

Step F: (S)-3-Cyclohexyl-2-(2-nitro-5-phenoxy-benzylidene)-hex-5-(Z)-enenitrile

To a solution of diisopropylamine (0.53 mL, 3.7 mmol) and N,N,N',N'-tetramethylethylenediamine (0.05 mL, 0.34 mmol) in tetrahydrofuran (2.0 mL) at −78° C. was added n-butyl lithium (2.0 M in cyclohexane, 1.9 mL, 3.7 mmol), dropwise, and the reaction mixture was stirred at 0° C. for 1 h. The reaction mixture was then cooled to −20° C. and treated with a solution of (R)-3-cyclohexyl-hex-5-enenitrile (300 mg, 1.7 mmol) in tetrahydrofuran (1 mL). The reaction mixture was stirred at this temperature for 2 h and then was cooled down to −78° C. and treated with a solution of 2-nitro-5-phenoxy-benzaldehyde (496 mg, 2.0 mol) in tetrahydrofuran (1 mL). The reaction mixture was stirred for 2 h while the temperature reached −30° C. The reaction mixture was quenched with saturated aqueous $NH_4Cl$ solution and then stirred overnight at room temperature. The reaction mixture was extracted with EtOAc and washed with brine. The organic layer was dried ($MgSO_4$) and concentrated to yield a residue which was purified by silica gel column chromatography (8:1 Hexanes:EtOAc) to yield (S)-3-cyclohexyl-2-(2-nitro-5-phenoxy-benzylidene)-hex-5-(Z)-enenitrile as the major isomer.

$MH^+$ 403.2

Step G: 3-((S)-1-Cyclohexyl-but-3-enyl)-6-phenoxy-quinolin-2-ylamine

To a solution of (S)-3-cyclohexyl-2-(2-nitro-5-phenoxy-benzylidene)-hex-5-(Z)-enenitrile (1.5 g, 3.7 mmol) in MeOH (20 mL) was added Zn (4.5 g, 68.8 mmol) and $NH_4Cl$ (510 mg, 9.5 mmol). The reaction mixture was heated to reflux overnight at 90° C. The reaction mixture was cooled to room temperature and filtered through Celite. The solid washed with MeOH (2×10 mL), and the combined filtrates were concentrated in vacuo to remove MeOH, and the residue was re-dissolved in $CHCl_3$. The organic layer washed with conc. $NH_4OH$ (3×20 mL) and dried ($MgSO_4$) to yield crude material. The crude material obtained after removal of solvent in vacuo was purified by silica gel column chromatography using 2:1 EtOAc:hexanes to yield 3-((S)-1-cyclohexyl-but-3-enyl)-6-phenoxy-quinolin-2-ylamine.

$MH^+$ 372.9

Step H: 4-(2-Amino-6-phenoxy-quinoline-3-yl)-4-(S)-cyclohexyl-butan-1-ol

To a solution of 3-((S)-1-cyclohexyl-but-3-enyl)-6-phenoxy-quinolin-2-ylamine (0.82 g, 2.2 mmol) in tetrahydrofuran (5.5 mL) at −20° C. was added 9-BBN (0.5 M in THF, 17.6 mL, 8.8 mol) dropwise over 20 min. The reaction mixture was stirred overnight while it reached room temperature. To the reaction mixture at 0° C. was then added aqueous 1N NaOH solution (8.2 mL) and aqueous 30% $H_2O_2$ solution (8.2 mL) and stirring was continued for 2.0 h. Water (15.0 mL) was added to the reaction mixture which was then extracted with EtOAc. The separated organic layer was dried ($MgSO_4$) and concentrated in vacuo to yield crude material. The crude material was purified by silica gel column chromatography using 10% MeOH in $CHCl_3$ to yield 4-(2-amino-6-phenoxy-quinoline-3-yl)-4-(S)-cyclohexyl-butan-1-ol.

$MH^+$ 390.9

Step I: 4-(2-Amino-6-phenoxy-quinoline-3-yl)-4-(S)-cyclohexyl-butyric acid

To an ice cold solution of 4-(2-amino-6-phenoxy-quinoline-3-yl)-4-(S)-cyclohexyl-butan-1-ol (0.44 g, 1.12 mmol) in acetone (15 mL) was added Jones reagent (0.7 M solution in a 0.12:1 mixture of concentrated $H_2SO_4$:$H_2O$, 16.0 mL, 11.3 mmol) dropwise, and the reaction mixture was stirred for 3.0 h. The excess reagent was quenched by adding isopropyl alcohol, and the resulting slurry was filtered through Celite®. The crude material obtained by removal of the solvent was purified by silica gel column chromatography using 30% MeOH in $CHCl_3$ to yield 4-(2-amino-6-phenoxy-quinoline-3-yl)-4-(S)-cyclohexyl-butyric acid.

$MH^+$ 404.9

Step J: 4-(2-Amino-6-phenoxy-quinolin-3-yl)-4-(S)-cyclohexyl-N-(3,3-dimethyl-butyl)-N-(1-methyl-1H-imidazol-2-ylmethyl)-butyramide To an ice cold solution of 4-(2-amino-6-phenoxy-quinoline-3-yl)-4-(S)-cyclohexyl-butyric acid (0.085 mg, 0.19 mmol) in dichloromethane (2.0 mL) was added isobutyl chloroformate (0.025 mL, 0.19 mmol) and N-methylmorpholine (0.021 mL, 0.019 mmol). The reaction mixture was stirred at this temperature for 0.5 h. The reaction mixture was then reacted with a solution of (3,3-dimethyl-butyl)-(1-methyl-1H-imidazole-2-ylmethyl)-amine (0.037 mg, 0.19 mmol) in dichloromethane (0.5 mL) and stirred at 0° C. for 0.5 h. To this reaction mixture was added CHCl₃, and the resulting mixture washed with H₂O and saturated aqueous NaHCO₃ solution. The organic layer was dried (MgSO₄) and concentrated in vacuo to yield crude material. The crude material was purified by silica gel column chromatography using 4% MeOH in CHCl₃ to yield 4-(2-amino-6-phenoxy-quinolin-3-yl)-4-(S)-cyclohexyl-N-(3,3-dimethyl-butyl)-N-(1-methyl-1H-imidazol-2-ylmethyl)-butyramide as a solid.

MH⁺ 583.0

$^1$H NMR (rotomers, 400 MHz, DMSO-d₆): δ 0.48 (s, 8.4H), 0.77 (s, 2.2H), 0.98 (bm, 9H), 1.53 (bm, 4.9H), 1.79 (bm, 3.8H), 2.10 (bm, 3.9H), 2.76 (bs, 1.3H), 2.97 (bs, 1.9H), 3.14 (bm, 0.6H), 3.34 (m, 1H), 3.52 (s, 3H), 4.36 (bs, 0.4H), 4.48 (m, 1.9H), 6.25 (bs, 1.9H), 6.69 (s, 0.2H), 6.78 (s, 1H), 6.99 (m, 2.4H), 7.10 (m, 2.1H), 7.20 (m, 2.2H), 7.37 (m, 2.4H), 7.48 (d, 1.3H), 7.77 (s, 1.2H), 8.33 (s, 0.3H)

Example 9

3-(2-Amino-6-phenoxy-3,4-dihydro-quinolin-3-yl)-N-cyclohexyl-N-methyl-propionamide

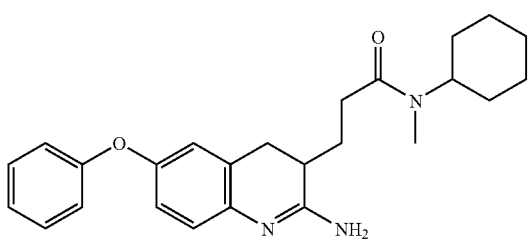

Step A: 2-cyano-hex-5-enoic acid ethyl ester

To a flamed dried flask charged with NaH (1.4 g, 35.46 mmol, 60% dispersion in mineral oil) and DMF (90 mL) equipped with a Firestone valve and under a stream of dry nitrogen was added, dropwise ethylcyanoacetate (3.14 mL, 29.56 mmol) over 20 min. The reaction mixture was then allowed to stir for 30 min, followed by addition of 4-bromobutene (3.0 mL, 29.56 mmol). The reaction mixture was allowed to stir overnight after which the solvent was removed by reduced pressure. The resulting crude mixture was dissolved in ethyl acetate, washed 3 times with 1N HCl solution and once with a saturated solution of brine. The organic and aqueous layers were separated and the organic layer was dried with sodium sulfate, filtered and the solvent was removed under reduced pressure to yield a residue. The residue was purified by flash chromatography using a mixture of 9:1 heptanes to ethyl acetate to yield a clear colorless oil.

$^1$H NMR (300 MHz, CDCl₃, δ5.8 (m, 1H); 5.1 (m, 2H); 4.25 (q, 2H, J=7.15 Hz); 3.55 (dd, 1H, J=6.59 Hz, J=6.35); 2.3 (m, 1H); 2.05 (m, 2H); 1.35 (t, 3H, J=7.14).

Step B: 2-nitro-5-phenoxy-phenyl-methanol 2-nitro-5-phenoxy-benzaldehyde (2.0 g, 8.22 mmol) was dissolved in methanol (20 mL) and cooled with an ice bath to 0° C. Sodium borohydride (0.9 g, 24.66 mmol) was added in 4 portions over 20 minutes and the reaction mixture was allowed to stir at 0° C. for one hour. A solution of sodium carbonate (10% w/v in water) was added to quench the reaction followed by pouring the crude reaction mixture into a separatory funnel with ethyl acetate. The organic layer washed 3 times with 10% sodium carbonate solution followed by one wash with saturated brine. The phases were separated and the organic layer was dried with sodium sulfate and filtered, and the ethyl acetate was removed under reduced pressure to yield the a white solid.

$^1$H NMR (300 MHz, CDCl₃, δ8.15 (d, 1H, J=9.07 Hz); 7.45 (m, 2H); 7.3 (m, 2H); 7.1 (m, 2H); 6.95 (dd, 1H, J=9.08 Hz, J=2.5 Hz). 5.0 (s, 2H); 2.55 (s, br, 1H).

Step C: 2-chloromethyl-1-nitro-4-phenoxy-benzene

To a round bottom flask equipped with a nitrogen inlet and a water cooled condenser, 2-nitro-5-phenoxy-phenyl-methanol (2.7 g, 11.1 mmol) and triethylamine (4.7 mL, 33.9 mmol) were dissolved in dichloromethane (100 mL). Methane sulfonyl chloride (2.6 mL, 33.3 mmol) was added to the reaction mixture which was subsequently heated to reflux for 16 h. The next day the reaction was removed from the heating source, allowed to cool and poured into a separatory funnel which contained a water solution of 1N HCl. The organic phase washed 2 times with 1N HCl and one time with saturated brine solution. The phases were separated and the ethyl acetate layer was dried with sodium sulfate, filtered and the solvent removed under reduced pressure to yield a residue. The residue was purified by flash chromatography using heptanes:ethyl acetate as the mobile phase (9:1) to yield a residue.

$^1$H NMR (300 MHz, CDCl₃, δ8.15 (d, 1H, J=9.07 Hz); 7.48 (m, 2H); 7.3 (m, 2H); 7.1 (m, 2H); 6.97 (dd, 1H, J=9.07, 2.7 Hz). 5.0 (s, 2H).

Step D: 2-cyano-2-(2-nitro-5-phenoxy-benzyl)-hex-5-enoic acid ethyl ester

To a round bottom flask equipped with a nitrogen inlet 2-cyano-hex-5-enoic acid ethyl ester (2.0 g, 11.96 mmol) and DMF (40 mL) were added. The reaction mixture was cooled to 0° C. followed by addition of NaH (0.48 g, 12.0 mmol, 60% dispersion in mineral oil). The reaction mixture was allowed to stir at 0° C. for another 5 min, followed by addition of 2-chloromethyl-1-nitro-4-phenoxy-benzene (2.6 g, 9.86 mmol). The reaction turned a dark purple color. After 3 h the reaction was quenched with 1N HCl, and the solvent was evaporated to yield crude mixture. The crude mixture was dissolved in ethyl acetate and washed 3 times with 1N HCl followed by a wash with saturated brine solution. The phases were separated, and the organic phase was dried with sodium sulfate and filtered, and the solvent was removed under reduced pressure to yield a residue. The residue was purified by flash chromatography using heptanes/ethyl acetate as the mobile phase 9:1 to yield a residue.

$^1$H NMR (300 MHz, CDCl₃, δ7.95 (m, 1H, J=9.07 Hz); 7.30 (m, 2H); 7.15 (m, 1H); 6.95 (m, 2H); 6.85 (m, 2H); 5.63 (m, 1H); 4.94 (m, 2H); 4.05 (m, 2H); 3.63 (d, 1H, J=13.97 Hz); 3.48 (d, 1H, J=13.97); 2.25 (m, 1H); 2.00 (m, 2H); 1.80 (m, 1H); 1.10 (t, 3H, 7.14)

Step E: 2-cyano-2-(2-nitro-5-phenoxy-benzyl)-hex-5-enoic acid 2-cyano-2-(2-nitro-5-phenoxy-benzyl)-hex-5-enoic acid ethyl ester (2.84 g, 7.20 mmol) was dissolved in methanol (42 mL). In a separate flask LiOH (1.5 g, 36.0 mmol) was dissolved in water (21 mL). The LiOH solution was added to the methanolic solution containing 2-cyano-2-(2-nitro-5-phenoxy-benzyl)-hex-5-enoic acid ethyl ester and the reaction was allowed to stir at room temperature for 2 hours. Next, 12N HCl (3 mL) was added to the reaction mixture followed by removal of the methanol under reduced pressure. The reaction mixture was poured into a separatory funnel, ethyl acetate was added and the organic layer washed 2 times with 1N HCl and one time with saturated brine solution. The organic layer was separated, dried with sodium sulfate, filtered and the solvent was removed to yield a residue.

$^1$H NMR (300 MHz, CDCl$_3$, δ8.80 (s, 1H, br) 8.10 (d, 1H, J=8.97 Hz); 7.45 (m, 2H); 7.30 (m, 1H); 7.10 (m, 2H); 7.0 (m, 2H); 5.80 (m, 1H); 5.10 (m, 2H); 3.72 (m, 2H); 2.42 (m, 1H); 2.22 (m, 2H); 2.0 (m, 2H).

Step F:
2-(2-nitro-5-phenoxy-benzyl)-hex-5-enenitrile

To a round bottom flask equipped with a stir bar, condenser, and a nitrogen inlet 2-cyano-2-(2-nitro-5-phenoxy-benzyl)-hex-5-enoic acid (4.0 g, 10.92 mmol) was added and dissolved in dimethylacetamide (10 mL). The solution was heated to 150° C. for 3 hours. The reaction mixture was allowed to room temperature, then the solvent was removed under reduced pressure. The resulting crude product was dissolved in ethyl acetate and washed 3 times with 1N HCl followed by one wash with saturated brine solution. The organic layer was separated and dried with anhydrous sodium sulfate and the solvent was removed to yield crude material. The crude material was subjected to flash chromatography (mobile phase 9:1 heptane:ethyl acetate) to yield a yellow oil.

$^1$H NMR (300 MHz, CDCl$_3$, δ8.80 (d, 1H, J=8.9 Hz); 7.5 (m, 2H); 7.30 (m, 1H); 7.15 (m, 2H); 7.00 (m, 2H); 5.85 (m, 1H); 5.10 (m, 2H); 3.45 (m, 1H); 3.10 (m, 1H); 2.90 (m, 1H); 2.35 (m, 2H) 1.85 (m, 2H).

Step G:
4-cyano-5-(2-nitro-5-phenoxy-phenyl)-pentanoic acid 2-(2-nitro-5-phenoxy-benzyl)-hex-5-enenitrile (1.07 g, 3.31 mmol) was dissolved in a mixture of acetonitrile (10 mL) and carbon tetrachloride (10 mL). In a separate vial sodium periodate (2.84 g, 13.28 mmol) was dissolved in water (15 mL) and this solution was added to the reaction mixture followed by ruthenium trichloride (0.021 g, 0.100 mmol). The reaction mixture was stirred vigorously for 16 h, and the next morning the reaction mixture was added to a separatory funnel with dichloromethane. The organic layer washed 3 times with 1N HCl and one time with saturated brine solution. The organic layer was dried with sodium sulfate, filtered and the solvent was removed under reduced pressure to yield a residue.

$^1$H NMR (300 MHz, CDCl$_3$, δ 8.07 (d, 1H, J=9.04 Hz); 7.4 (m, 2H); 7.20 (m, 1H); 7.05 (m, 2H); 6.90 (m, 2H); 3.35 (m, 1H); 3.15 (m, 1H); 2.85 (m, 1H); 2.55 (m, 2H); 2.0 (m, 2H).

Step H: 4-cyano-5-(2-nitro-5-phenoxy-phenyl)-pentanoic acid cyclohexyl-methyl-amide 4-cyano-5-(2-nitro-5-phenoxy-phenyl)-pentanoic acid (0.230 g, 0.68 mmol) was dissolved in dichloromethane (1.5 mL) followed by addition of HOBt (0.103 g, 0.68 mmol), triethylamine (0.170 mL, 0.68 mmol), EDC (0.194 g, 1.01 mmol) and N-methyl-cyclohexylamine (0.09 mL, 0.68 mmol). The reaction was allowed to proceed for 16 h after which time, the solvent was removed under reduced pressure. The resulting mixture was dissolved in ethyl acetate and washed 3 times with 10% sodium carbonate solution, one time with saturated brine solution, 3 times with 1N HCl and then again one time with brine wash. The organic layer was dried with anhydrous sodium sulfate and the solvent was removed under reduced pressure to yield a residue. The residue was purified with flash chromatography using a mixture of 65:35 heptanes:ethyl acetate as the mobile phase to yield a residue.

$^1$H NMR (300 MHz, CDCl$_3$, δ8.24 (d, 1H, J=9.09 Hz); 7.55 (m, 2H); 7.39 (m, 1H); 7.22 (m, 1H); 7.12 (m, 1H); 7.05 (m, 1H); 4.55 (m, 1H); 3.60 (m, 1H); 3.50 (dd, 1H, J=4.92 Hz; 13.01 Hz); 3.35 (m, 1H); 3.10 (m, 1H); 3.60 (m, 1H); 2.95 (m, 3H); 2.65 (m, 2H); 2.30 (m, 1H); 2.10 (m, 1H); 1.90 (m, 1H); 1.70 (m, 2H); 1.68 (m, 1H); 1.50 (m, 2H); 1.23 (m, 1H).

Step I: 5-(2-amino-5-phenoxy-phenyl)-4cyano-pentanoic acid cyclohexyl-methyl-amide 4-cyano-5-(2-nitro-5-phenoxy-phenyl)-pentanoic acid cyclohexyl-methyl-amide (0.200 g, 0.46 mmol), ammonium chloride (0.31 g, 5.75 mmol) and methanol (3.0 mL) were added to a round bottom flask followed by addition of powdered zinc (0.4 g). The vessel was equipped with a condenser and the reaction was headed to reflux for 2 h followed by filtration through a pad of Celite®. The solvent was removed and the resulting residue was dissolved in ethyl acetate, then washed 3 times with 10% sodium carbonate solution. The organic layer was dried with sodium sulfate, filtered and the solvent was removed under reduced pressure. The resulting residue was used in subsequent steps without further purification.

LC-MS m/z calculated for $C_{25}H_{31}N_3O_2$ 405.53 (M) Measured 406.66 (M+H)$^+$; t$_r$=3.50 min.

Step J: 3-(2-Amino-6-phenoxy-3,4-dihydro-quinolin-3-yl)-N-cyclohexyl-N-methyl-propionamide 5-(2-amino-5-phenoxy-phenyl)-4-cyano-pentanoic acid cyclohexyl-methyl-amide (0.20 g, 0.46 mmol) was dissolved in toluene (5 mL), followed by addition of aluminum chloride (0.184 g, 1.38 mmol). The reaction mixture was heated to reflux for 10 minutes and then allowed to cool to room temperature. The crude reaction mixture was poured into a separatory funnel and partitioned between ethyl acetate and 10% Na$_2$CO$_3$ solution. The organic layer was washed 2 more times with 10% Na$_2$CO$_3$ solution and one time with saturated brine solution. The organic layer was dried with anhydrous sodium sulfate and the solvent was removed under reduced pressure to yield a residue which was purified by flash chromatography using chloroform:methanol:triethylamine as the mobile phase to yield the title compound as a residue.

$^1$H NMR (300 MHz, CDCl$_3$, δ 7.35 (m, 1H); 7.30 (s, 1H); 7.10 (m, 1H); 7.05 (m, 2H); 7.02 (s, 1H); 6.90 (m, 1H); 6.80 (m, 1H); 4.45 (m, 0.5H); 3.60 (m, 0.5H); 3.10 (m 1H); 2.86 (s, 1.5H); 2.85 (s, 1.5H); 2.75 (m, 1H); 2.45 (m, 3H); 2.0-1.1 (m, 10H).

LC-MS m/z calculated for $C_{25}H_{31}N_3O_2$ 405.53 (M) Measured as 406.67 (M+H)$^+$; t$_r$=3.20 min.

Additional compounds of the present invention were similarly prepared according to the procedures and schemes described herein, selecting and substituting suitably substituted reagents and starting materials.

Example 10

In Vitro BACE FS1% Inhibition Assay

The following reagents were used in this assay: sodium acetate, PEG8000 (Sigma), DMSO, HEPES, FS1 substrate

[R(AedensE)EEVNLDAEFK-(DabcylK)R], β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 μg/mL. The β-secretase (BACE) working solution was prepared by diluting a 0.83 mg/mL BACE stock solution with enzyme assay buffer to a final concentration of 4 μg/mL.

Test compounds were dissolved in DMSO to 10 mM. Compounds were further diluted in vehicle to various concentrations in the range of 405 μM to 4.05 μM (13.5×final compound concentration in screening plate).

The screening procedure for this assay was as follows: 15 μL of BACE working solution was pipetted into each well of a 96-well plate. To each well was then pipetted 2 μL of test compound at the selected concentration. Test compound and BACE were then mixed with a pipettor and incubated for 20 min at room temperature. To each well was then added 10 μL of the FS1 substrate working solution. The plates were then incubated for 1 hour at room temperature. The fluorescence for each well was then measured on an LJL analyst (Ex 360 nm/Em 530 nm).

The procedure for the blank (negative control) was as follows. 15 μL of assay buffer was pipetted into each well to be used as a blank control. To each well was then added 2 μL of vehicle and 10 μL of FS1-substrate working solution. The plates were then incubated for 1 hour at room temperature. The fluorescence was measured on an LJL analyst (Ex 360 nm/Em 530 nm).

The procedure for the positive control was as follows: 15 μL of BACE working solution was pipetted into each well to be used as a positive control. To each well was then pipetted 2 μL of vehicle. Vehicle and BACE were then mixed with a pipettor and incubated for 20 min at room temperature. To each well was then added 10 μL of the FS1 substrate working solution. The plates were then incubated for 1 hour at room temperature. The fluorescence (Fl) was then measured on an LJL analyst (Ex 360 nm/Em 530 nm).

For test compounds, % inhibition was determined at each concentration as follows:

$$\% \text{ Inhibition} = \left[1 - \left(\frac{[Fl(\text{compound}) - Fl(\text{negative control})]}{[Fl(\text{positive control}) - Fl(\text{negative control})]}\right)\right] \times 100\%$$

% Inhibition values of less than 30% were indistinguishable from control and are listed as ≦30% in the Table below. % Inhibition values greater than 100% were indistinguishable from 100% within the error of the measurement.

Example 11

In Vitro BACE Assay

The following reagents were used in this assay: sodium acetate, PEG8000 (Sigma), DMSO, HEPES, FS1 substrate [R(AedensE)EEVNLDAEFK-(DabcylK)R], β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 μg/mL. The β-secretase (BACE) working solution was prepared by diluting a 0.83 mg/mL BACE stock solution with enzyme assay buffer to a final concentration of 4 μg/mL.

Test compounds were dissolved in DMSO at 10 mM. Compounds were further diluted in compound vehicle to various concentrations in the range of 675 μM to 13.5 nM (13.5×final compound concentration in Ki plate).

The procedure for this assay was as follows: 15 μL of BACE working solution was pipetted into each well of a 96-well plate. To each well was then pipetted 2 μL of test compound at the selected concentration. Test compound and BACE were then mixed with a pipettor and incubated for 20 min at room temperature. To each well was then added 10 μL of the FS1 substrate working solution. The fluorescence for each well was then measured on a Polarstar fluorometer (Ex 390 nm/Em 520 nm) for 20 min at room temperature, reading fluorescence at 1 min intervals.

The procedure for the positive control was as follows: 15 μL of BACE working solution was pipetted into each well to be used as a positive control. To each well was then pipetted 2 μL of vehicle. Vehicle and BACE were then mixed with a pipettor and incubated for 20 min at room temperature. To each well was then added 10 μL of the FS1 substrate working solution. The fluorescence was then measured on a Polarstar fluorometer (Ex 390 nm/Em 520 nm) for 20 min at room temperature, reading fluorescence at 1 min intervals.

For test compounds, $K_i$ inhibition was determined as follows: For each compound concentration and positive control, rate of cleavage of substrate ($V_i$, where i=compound concentration in μM) was determined as Δ Fluorescence/Δ time (min). Cleavage rates ($V_i$) were plotted as a function of inhibitor concentration in μM [I]. The $K_i$ was then determined by fitting the following equation to the graph of [I] vs $V_i$ $$Y = aV_{max}/(50 + 24*(1 + X/K_i)),$$

where 50=substrate concentration (μM) and 24=$K_m$ of substrate (μM).

Representative compounds of the present invention were tested according to procedures described in Examples 10 and 11 above, with results as listed in Table 6, below. Because the % Inhibition assay detects changes in fluorescence, negative values are possible. % Inhibition values of less than about 25% (including negative values) are within the noise or error of the procedures as described.

TABLE 6

BACE in vitro Assay

| ID No. | % Inhibition (Example 10) @ 3 µM | @ 1 µM | @ 0.3 µM | (Example 11) Ki (µM) |
|---|---|---|---|---|
| 2 | 107 | 78 | 45 | 0.23 |
| 3 | 115 | 89 | 58 | 0.49 |
| 4 | 42 | 9 | 14 | |
| 5 | 37 | 41 | 22 | |
| 6 | −5 | −4 | −11 | |
| 7 | −6 | −7 | −28 | |
| 8 | 31 | −21 | −28 | |
| 9 | 80 | 35 | 16 | |
| 10 | −0.3 | −13 | −11 | |
| 11 | 81 | 5 | −6 | |
| 12 | 19 | 0.8 | −2 | |
| 13 | 88 | 42 | 2 | 0.64 |
| 14 | −15 | −27 | −14 | |
| 15 | 78 | 58 | 43 | 0.28 |
| 16 | 78 | 27 | 29 | 0.44 |
| 17 | 46 | 20 | 19 | |
| 18 | 36 | 26 | 29 | |
| 19 | 24 | −7 | −15 | |
| 20 | 34 | −11 | −8 | |
| 21 | 10 | −1 | 0.5 | |
| 22 | −3 | −19 | 0.6 | |
| 23 | 127, 125 | 88, 93 | 34, 64 | 0.12, 0.31 |
| 24 | 132 | 103 | 56 | 0.066 |
| 25 | 126 | 114 | 83 | 0.16 |
| 26 | 32 | 21 | 21 | |
| 75 | 17 | −8 | 24 | |
| 76 | 16 | −7 | 28 | |
| 101 | | | | 0.10 |
| 104 | −4 | −15 | −11 | |
| 105 | 10 | −2 | −14 | |
| 106 | 48 | 14 | 4 | |
| 107 | 1 | 4 | 1 | |
| 108 | −0.3 | 4 | −4 | |
| 503 | 36 | 19 | 28 | |
| 504 | 18 | 21 | 21 | |

Test compounds were dissolved in DMSO to 10 mM. Compounds were further diluted in vehicle to various concentrations in the range of 405 µM to 4.05 µM (13.5×final compound concentration in screening plate).

The screening procedure for this assay was as follows: 15 µL of BACE working solution was pipetted into each well of a 96-well plate. To each well was then pipetted 2 µL of test compound at the selected concentration. Test compound and BACE were then mixed with a pipettor and incubated for 20 min at room temperature. To each well was then added 10 µL of the substrate working solution. The plates were then incubated for 1 hour at room temperature. The fluorescence for each well was then measured on an LJL analyst (Ex 360 nm/Em 530 nm).

The procedure for the blank (negative control) was as follows. 15 µL of assay buffer was pipetted into each well to be used as a blank control. To each well was then added 2 µL of vehicle and 10 µL of substrate working solution. The plates were then incubated for 1 hour at room temperature. The fluorescence was measured on an LJL analyst (Ex 360 nm/Em 530 nm).

The procedure for the positive control was as follows: 15 µl of BACE working solution was pipetted into each well to be used as a positive control. To each well was then pipetted 2 µL of vehicle. Vehicle and BACE were then mixed with a pipettor and incubated for 20 min at room temperature. To each well was then added 10 µL of the substrate working solution. The plates were then incubated for 1 hour at room temperature. The fluorescence (Fl) was then measured on an LJL analyst (Ex 360 nm/Em 530 nm).

For test compounds, % inhibition was determined at each concentration as follows:

$$\% \text{ Inhibition} = \left[1 - \left(\frac{[Fl(\text{compound}) - Fl(\text{negative control})]}{[Fl(\text{positive control}) - Fl(\text{negative control})]}\right)\right] \times 100\%$$

Example 12

In Vitro BACE % Inhibition Assay

The following reagents were used in this assay: sodium acetate, PEG8000 (Sigma), DMSO, HEPES, (Aedens)-EVNLDAEF-(Dabcyl K-amide) substrate, β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The substrate stock solution was prepared in DMSO as a 10 mg/mL solution. The substrate working solution was prepared by diluting the 10 mg/mL stock solution with substrate assay buffer to a final concentration of 300 µg/mL. The β-secretase (BACE) working solution was prepared by diluting a 0.83 mg/mL BACE stock solution with enzyme assay buffer to a final concentration of 4 µg/mL.

% Inhibition values of less than 30% were indistinguishable from control and are listed as ≦30% in the Table below.

Representative compounds of the present invention were tested according to procedure described in Example 12 above with results as listed in Table 7 below. Because the % Inhibition assay detects changes in fluorescence, negative values are possible. % Inhibition values of less than about 25% (including negative values) are within the noise or error of the procedures as described.

TABLE 7

| ID No | % Inhibition 30 µM | 10 µM | 3 µM |
|---|---|---|---|
| 1 | | 9 | −8.5 |
| 101 | Ki = 0.28 | | |
| 500 | | −82 | −19 |
| 501 | | −36 | 12 |
| 502 | | −16 | −8 |

Example 13

In Vitro BACE IC$_{50}$ Assay

The following standards are reagents were used in this assay: Sodium Citrate trisodium salt dihydrate (Sigma), Citric Acid monohydrate (Merck), PEG8000 (Sigma), MCA-substrate (Bachem), β-secretase (BACE) (Panvera), 96-well black plate (Costar (Elscolab)), StatVal (Bachem). The standard assay buffer solution prepared and used in this assay is as follows: 0.05 M, pH 5.0 mixture of sodium citrate trisodium salt dihydrate (9.56 g), citric acid monohydrate (3.68 g) and PEG8000 (0.50 g). The MCA-substrate stock solution was prepared by mixing 10 mg MCA-substrate with 5 mL DMSO for a final solution concentration of 2.0 mg/mL. The substrate work solution was prepared by mixing 0.1 mL substrate in 1.90 mL assay buffer for a final concentration of 0.05 mM. The β-secretase (BACE) working solution was prepared by mixing 8 μL BACE in 2 mL assay buffer for a final concentration of 10 μg/mL. Test compounds were dissolved in DMSO at various concentrations in the range of $3.3 \times 10^{-3}$ M to $1.5 \times 10^{-6}$ M.

Briefly, the procedure for this BACE IC$_{50}$ assay was as follows. 60 μL of assay buffer was pipetted into each well of a 96-well plate. To each well was then pipetted 1 μL of test compound at the selected concentration. To each well was then added 20 μL of the β-secretase working solution and 20 μL of the MCA-substrate stock solution. Each well was mixed for a few seconds and the $T_0$ measured with a Fluoroscan Ex320/Em405. The plates were then incubated for 1 hour at room temperature and the $T_{60}$ measured with the Fluoroscan Ex 320 nm/Em 405 nm.

The procedure for the blank (reference well) was as follows. 80 μL of assay buffer was pipetted into each well to be used as a blank control. To each well was then added 1 μL of DMSO and 20 μL of MCA-substrate solution in each well. The $T_0$ was measured with the Fluoroscan Ex 320 nm/Em 405 nm, the plate was incubated for 1 hour at room temperature and the $T_{60}$ was then measured with the Fluoroscan Ex 320 nm/Em 405 nm.

The procedure for the positive control was as follows. 60 μL of assay buffer was pipetted into each well to be used as a positive control. To each well was then added 1 μL of DMSO, 20 μL of BACE working solution and 20 μL of MCA-substrate stock solution. The $T_0$ was measured with the Fluoroscan Ex 320 nm/Em 405 nm, the plate was incubated for 1 hour at room temperature and the $T_{60}$ was then measured with the Fluoroscan Ex 320 nm/Em 405 nm.

For test compounds, measured at multiple concentrations, the measured $T_0$ and $T_{60}$ values were used to calculate an IC$_{50}$ value using Graphpad Software (or PIR).

Representative compounds of the present invention were measured for BACE inhibition according to the procedure described in Example 13 above, with results as listed in Table 8 below.

TABLE 8

| ID No | IC$_{50}$ (μM) |
| --- | --- |
| 102 | 0.17 |
| 103 | 0.22 |

Example 14

In Vitro BACE Assay

This assay was run by CEREP (Catalog Ref. 761-B, Referred to SOP No. 1C131; ERMOLIEFF, J., LOY, J. A., KOELSCH, G. and TANG, J., Proteolytic activation of recombinant pro-memapsin 2 (pro-BACE) studied with new fluorogenic substrates, Biochemistry, (2000) Vol. 39, p. 12450).

More specifically the assay, run at 50 μL in a 96 well plate, evaluated the effect of test compound on the activity of the human BACE-1 quantified by measuring the formation of Mca-S-E-V-N-L-NH$_2$ from Mca-S-E-V-N-L-D-A-E-F-R-K(Dnp)-R-R-NH$_2$, using a recombinant enzyme.

The test compound, reference compound or water (control) was added to a buffer containing 0.09 M sodium acetate (pH 4.5) and 0.25 μg BACE-1. Compound interference with the fluorimetric detection method due to autofluorescence was then checked by measurements at the wavelengths defined to evaluate the enzyme activity. Thereafter, the reaction was initiated by adding 7.5 μM of the substrate Mca-S-E-V-N-L-D-A-E-F-R-K(Dnp)-R-R-NH$_2$ and the mixture was incubated for 60 min at 37° C. For control basal measurement, the substrate was omitted from the reaction mixture. Immediately after the incubation, the fluorescence intensity emitted by the reaction product Mca-S-E-V-N-L-NH$_2$ was measured at $\lambda ex=320$ nm and $\lambda em=405$ nm using a microplate reader (Ultra, Tecan). The standard inhibitory reference compound was OM99-2, which was tested in each experiment at several concentrations to obtain an inhibition curve from which its IC$_{50}$ value was calculated.

Representative compounds of the present invention were tested according to procedure described in Example 14 above with results as listed in Table 9 below.

TABLE 9

| | % Inhibition and IC$_{50}$ | | |
| --- | --- | --- | --- |
| ID No | 1 μM | 0.3 μM | IC$_{50}$ (μM) |
| 16 | 46 | 15 | 0.7 |
| 23 | 78 | | 0.42 |
| 30 | 91 | | 0.41 |
| 31 | 59 | 32 | 0.74 |
| 33 | | 14 | |
| 36 | 59 | 49 | 0.61 |
| 37 | 81 | 27 | 0.58 |
| 38 | 9 | 8 | |
| 39 | | 16 | 0.49 |
| 40 | 54 | 13 | 0.65 |
| 41 | 79 | 11 | 0.47 |
| 42 | 58 | | 0.81 |
| 43 | 88 | | 0.65 |
| 44 | −1 | | |
| 45 | 46 | | 1.1 |
| 48 | 19 | | |
| 49 | 86 | | |
| 50 | 87 | | 0.74 |
| 51 | 56 | | 1.2 |
| 52 | 6 | | |
| 53 | 90 | | 0.46 |
| 54 | 85 | | 0.45 |
| 55 | 83 | | 0.42 |
| 56 | 94 | | |
| 57 | 93 | | |
| 58 | 88 | | |
| 59 | 78 | | |
| 60 | 83 | | 0.32 |
| 61 | 15 | | |
| 62 | 0 | | |
| 63 | 7 | | |

TABLE 9-continued

| | % Inhibition and IC$_{50}$ | | |
|---|---|---|---|
| ID No | 1 µM | 0.3 µM | IC$_{50}$ (µM) |
| 64 | 83 | | 0.19 |
| 65 | 69 | | 0.85 |
| 66 | 86 | | 0.47 |
| 67 | 90 | | 0.41 |
| 68 | 41 | | 1.5 |
| 69 | 69 | | 0.67 |
| 70 | 10 | | |
| 71 | 73 | | |
| 72 | 81 | | |
| 509 | −3 | 11 | |

Representative compounds of the present invention were further tested in various cellular assays. The measured results in these assays were generally consistent with the in vitro results listed above.

Example 15

In Vivo Testing

Compounds of the present invention may be further tested for their effectiveness in the treatment of disorders mediated by the BACE enzyme, for example Alzheimer's disease, by testing the compounds in an in vivo assay, for example, as disclosed in Sirinathsinghji, D. J. S. (Merck Sharp and Dohme Research Laboratories, Neuroscience Research Centre, Essex, UK.), *Transgenic mouse models of Alzheimer's disease*, Biochemical Society Transactions (1998), 26(3), pp 504-508;

Van Leuven, F. (Experimental Genetics Group, Center for Human Genetics, Flemish Institute for Biotechnology (VIB), K. U. Leuven, Louvain, Belg.), *Single and multiple transgenic mice as models for Alzheimer's disease*, Progress in Neurobiology (Oxford) (2000), 61(3), pp 305-312;

Hsiao, K.; Chapman, P.; Nilsen, S.; Eckman, C.; Harigaya, Y.; Younkin, S.; Yang, F.; Cole, G. (Dep. Neurology, Univ. Minnesota, Minneapolis, Minn., USA), *Correlative memory deficits, Aβ elevation, and amyloid plaques in transgenic mice*, Science (Washington, D.C.) (1996), 274 (5284), pp 99-102 (Tg2576 mice);

Oddo, S.; Caccamo, A.; Shepherd, J. D.; Murphy, M. P.; Golde, T. E.; Kayed, R.; Metherate, R.; Mattson, M. P.; Akbari, Y.; LaFerla, F. M. (Department of Neurobiology and Behavior, University of California, Irvine, Irvine, Calif., USA), *Triple-transgenic model of Alzheimer's disease with plaques and tangles: Intracellular Aβ and synaptic dysfunction*, Neuron (2003), 39(3), pp 409-421 (APP Triple Transgenic Mice);

Ruberti, F.; Capsoni, S.; Comparini, A.; Di Daniel, E.; Franzot, J.; Gonfloni, S.; Rossi, G.; Berardi, N.; Cattaneo, A. (Neuroscience Program, International School for Advanced Studies (SISSA), Trieste, Italy), *Phenotypic knockout of nerve growth factor in adult transgenic mice reveals severe deficits in basal forebrain cholinergic neurons, cell death in the spleen, and skeletal muscle dystrophy*, Journal of Neuroscience (2000), 20(7), pp 2589-2601 (AD11 mice);

Games, D.; Adams, D.; Alessandrini, R.; Barbour, R.; Berthelette, P.; Blackwell, C.; Carr, T.; Clemens, J.; Donaldson, T.; et al. (Athena Neurosciences, Inc., South San Francisco, Calif., USA), *Alzheimer-type neuropathology in transgenic mice overexpressing V717F β-amyloid precursor protein*, Nature (London) (1995), 373(6514), pp 523-7 (V717F mice);

Neve, R. L.; Boyce, F. M.; McPhie, D. L.; Greenan, J.; Oster-Granite, M. L. (Dep. Genetics, Harvard Medical School and McLean Hospital, Belmont, Mass., USA), *Transgenic mice expressing APP-C100 in the brain*, Neurobiology of Aging (1996), 17(2), pp 191-203 (APP-C100 mice);

and/or as disclosed in U.S. Pat. No. 5,811,633; U.S. Pat. No. 5,877,399; U.S. Pat. No. 5,672,805; U.S. Pat. No. 5,720, 936; U.S. Pat. No. 5,612,486; U.S. Pat. No. 5,580,003; U.S. Pat. No. 5,850,003; U.S. Pat. No. 5,387,742; U.S. Pat. No. 5,877,015; U.S. Pat. No. 5,811,633; U.S. Pat. No. 6,037, 521; U.S. Pat. No. 6,184,435; U.S. Pat. No. 6,187,922; U.S. Pat. No. 6,211,428; and U.S. Pat. No. 6,340,783.

Example 16

Human Testing

Compounds of the present invention may be further tested for their effectiveness in the treatment of disorders mediated by the BACE enzyme, for example Alzheimer's disease, by testing the compounds in human subjects, for example, as disclosed in Lins, H.; Wichart, I.; Bancher, C.; Wallesch, C.-W.; Jellinger, K. A.; Roesler, N. (Department of Neurology, Otto-von-Guericke-University, Magdeburg, Germany), *Immunoreactivities of amyloid βpeptide(1-42) and total τ protein in lumbar cerebrospinal fluid of patients with normal pressure hydrocephalus*, Journal of Neural Transmission (2004), 111(3), pp 273-280;

Lewczuk, P.; Esselmann, H.; Otto, M.; Maler, J. M.; Henkel, A. W.; Henkel, M. K.; Eikenberg, O.; Antz, C.; Krause, W.-R.; Reulbach, U.; Kornhuber, J.; Wiltfang, J. (Department of Psychiatry and Psychotherapy, Molecular Neurobiology Lab, University of Erlangen-Nuremberg, Erlangen, Germany), *Neurochemical diagnosis of Alzheimer's dementia by CSF Aβ42, Aβ42/Aβ40 ratio and total tau*, Neurobiology of Aging (2004), 25(3), pp 273-281;

Olsson, A.; Hoglund, K.; Sjogren, M.; Andreasen, N.; Minthon, L.; Lannfelt, L.; Buerger, K.; Moller, H.-J.; Hampel, H.; Davidsson, P.; Blennow, K. (Sahlgrenska University Hospital, Experimental Neuroscience Section, Institute of Clinical Neuroscience, Goteborg University, Moelndal, Sweden), *Measurement of α- and β-secretase cleaved amyloid precursor protein in cerebrospinal fluid from Alzheimer patients*, Experimental Neurology (2003), 183 (1), pp 74-80;

Wahlund, L.-O.; Blennow, K. (Karolinska Institute, Section of Geriatric Medicine, Department of Clinical Neuroscience and Family Medicine, Huddinge University Hospital, Stockholm, Sweden), *Cerebrospinal fluid biomarkers for disease stage and intensity in cognitively impaired patients*, Neuroscience Letters (2003), 339(2), pp 99-102;

El Mouedden, M., Vandermeeren, M., Meert, T., Mercken, M. (Johnson & Johnson Pharmaceutical Research and Development, Division of Janssen Pharmaceutica N.V., Turnhoutseweg 30, Beerse, Belg.), *Development of a specific ELISA for the quantitative study of amino-terminally truncated beta-amyloid peptides*, Journal of Neuroscience Methods (2005), 145(1-2), pp 97-105;

Vanderstichele, H., Van Kerschaver, E., Hesse, C., Davidsson, P., Buyse, M.-A., Andreasen, N., Minthon, L., Wallin, A., Blennow, K., Vanmechelen, E., (Innogenetics NV, Ghent, Belg.), Standardization of measurement of β-amyloid(1-42) in cerebrospinal fluid and plasma, Amyloid (2000), 7(4), pp 245-258;

and/or Schoonenboom, N. S., Mulder, C., Van Kamp, G. J., Mehta, S. P., Scheltens, P., Blankenstein, M. A., Mehta, P. D., Amyloid β 38, 40, and 42 species in cerebrospinal fluid: More of the same?, Annals of Neurology (2005), 58(1), pp 139-142.

Example 17

As a specific embodiment of an oral composition, 100 mg of the compound prepared as in Example 8 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (II)

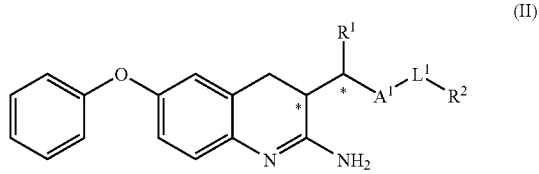

(II)

wherein
$R^1$ is selected from the group consisting of hydrogen, $C_{1-8}$alkyl, hydroxy substituted $C_{2-8}$alkyl, $NR^A R^B$ substituted —$C_{2-8}$alkyl, —$C_{1-4}$alkyl-O—$C_{1-4}$alkyl, cycloalkyl, —($C_{1-4}$alkyl)-cycloalkyl, heterocycloalkyl and —($C_{1-4}$alkyl)-(heterocycloalkyl); wherein $R^A$ and $R^B$ are each independently selected from the group consisting of hydrogen and $C_{1-4}$alkyl;

provided that when $R^1$ is hydroxy substituted $C_{2-8}$alkyl or $NR^A R^B$ substituted —$C_{2-8}$alkyl, then the hydroxy or $NR^A R^B$ group is not bound to the alpha carbon;

$A^1$ is selected from the group consisting of —$C_{1-4}$alkyl-;

$L^1$ is selected from the group consisting of —$NR^C$—, —$NR^C$—C(O)— and —C(O)—$NR^C$—; wherein $R^C$ is selected from the group consisting of hydrogen, $C_{1-6}$alkyl, hydroxy substituted $C_{1-4}$alkyl and $C_{5-7}$cycloalkyl;

$R^2$ is selected from the group consisting of $C_{1-8}$alkyl, $C_{2-12}$alkenyl, —$C_{1-4}$alkyl-O—$C_{1-4}$alkyl, —$C_{1-4}$alkyl-$NR^D R^E$, —$C_{1-4}$alkyl-OH, cycloalkyl, —$C_{1-4}$alkyl-cycloalkyl, partially unsaturated carbocyclyl, —$C_{1-4}$alkyl-(partially unsaturated carbocyclyl), aryl, aralkyl, heteroaryl, —$C_{1-4}$alkyl-heteroaryl, heterocycloalkyl, —$C_{1-4}$alkyl-heterocycloalkyl and —CH($R^3$)—CH$_2$—$R^4$;

wherein the cycloalkyl, partially unsaturated carbocyclyl, aryl, heteroaryl or heterocycloalkyl, whether alone or as part of a substituent group, is optionally substituted from one or more substituents independently selected from the group consisting of $C_{1-4}$alkyl, —$C_{1-4}$alkyl-O—$C_{1-4}$alkyl, carboxy, —C(O)O—$C_{1-4}$alkyl and aralkyl;

wherein $R^D$ and $R^E$ are each independently selected from the group consisting of hydrogen and $C_{1-4}$alkyl;

wherein $R^3$ is selected from the group consisting of $C_{1-4}$alkyl-cycloalkyl, —CO$_2$H, —C(O)O—$C_{1-4}$alkyl and —C(O)$NR^F R^G$; wherein $R^F$ and $R^G$ are each independently selected from the group consisting of hydrogen and $C_{1-4}$alkyl; alternatively, $R^F$ and $R^G$ are taken together with the nitrogen atom to which they are bound to form a 5 to 6 membered heteroaryl or heterocycloalkyl group;

wherein $R^4$ is selected from the group consisting of hydroxy and $C_{1-4}$alkoxy;

alternatively, when $L^1$ is selected from the group consisting of —$NR^C$— and —C(O)—$NR^C$—, $R^C$ and $R^2$ are taken together with the nitrogen atom to which they are bound to form a ring structure selected from the group consisting of 1-piperidinyl, 1-piperazinyl, 4-morpholinyl, 1-pyrrolidinyl, 1-pyrazalidinyl and 1-azepanyl;

wherein the piperidinyl, piperazinyl or morpholinyl is optionally substituted with one or more substituents independently selected from $C_{1-4}$alkyl or —$C_{1-3}$alkyl-C(O)—$NR^J R^K$; wherein $R^J$ and $R^K$ are each independently selected form hydrogen or $C_{1-4}$alkyl; alternatively, $R^J$ and $R^K$ are taken together with the nitrogen atom to which they are bound to form a heteroaryl or heterocycloalkyl;

or a pharmaceutically acceptable salt thereof.

2. A compound as in claim 1 wherein
$R^1$ is selected from the group consisting of hydrogen, $C_{1-4}$alkyl, hydroxy substituted $C_{2-4}$alkyl, $NR^A R^B$ substituted —$C_{2-4}$alkyl, —$C_{1-2}$alkyl-O—$C_{1-4}$alkyl, $C_{5-7}$cycloalkyl, —($C_{1-2}$alkyl)-($C_{5-7}$cycloalkyl), 5 to 7 membered heterocycloalkyl and —($C_{1-2}$alkyl)-(5 to 7 membered heterocycloalkyl); wherein $R^A$ and $R^B$ are each independently selected from the group consisting of hydrogen and $C_{1-2}$alkyl;

provided that when $R^1$ is hydroxy substituted $C_{2-4}$alkyl or $NR^A R^B$ substituted —$C_{2-4}$alkyl, then the hydroxy or $NR^A R^B$ group is not bound to the alpha carbon;

$A^1$ is selected from the group consisting of —$C_{1-3}$alkyl-;

$L^1$ is selected from the group consisting of —$NR^C$—C(O)— and —C(O)—$NR^C$—; wherein $R^C$ is selected from the group consisting of hydrogen, $C_{1-4}$alkyl and $C_{5-7}$cycloalkyl;

$R^2$ is selected from the group consisting of $C_{1-8}$alkyl, $C_{2-12}$alkenyl, —$C_{1-4}$alkyl-$NR^D R^E$, cycloalkyl, —$C_{1-4}$alkyl-cycloalkyl, heterocycloalkyl and —$C_{1-4}$alkyl-heterocycloalkyl;

wherein the cycloalkyl or heterocycloalkyl, whether alone or as part of a substituent group, is optionally substituted with one to two substituents independently selected from the group consisting of $C_{1-4}$alkyl, —$C_{1-4}$alkyl-O—$C_{1-4}$alkyl, carboxy and —C(O)O—$C_{1-4}$alkyl;

wherein $R^D$ and $R^E$ are each independently selected from the group consisting of hydrogen and $C_{1-2}$alkyl;

alternatively, when $L^1$ is —C(O)—N($R^C$)—; $R^C$ and $R^2$ are taken together with the nitrogen atom to which they are bound to form a ring structure selected from the group consisting of 1-piperidinyl, 1-piperazinyl and 4-morpholinyl;

wherein the piperidinyl, piperazinyl or morpholinyl is optionally substituted with —$C_{1-3}$alkyl-C(O)$NR^J R^K$; wherein $R^J$ and $R^K$ are each independently selected form hydrogen or $C_{1-4}$alkyl; alternatively, $R^J$; and $R^K$ are taken together with the nitrogen atom to which they are bound to form a 5-7 membered heterocycloalkyl;

or a pharmaceutically acceptable salt thereof.

3. A compound as in claim 2 wherein $R^1$ is hydrogen;

$A^1$ is —$CH_2$—;

$R^2$ is selected from the group consisting of $C_{1-4}$alkyl, cycloalkyl and 5 to 7 membered heterocycloalkyl; wherein the 5 to 7 membered heterocycloalkyl is optionally substituted with a substituent selected from $C_{1-4}$alkyl;

alternatively, when $L^1$ is —C(O)—N($R^C$)—; $R^C$ and $R^2$ are taken together with the nitrogen atom to which they are bound to form a ring structure selected from the group consisting of 1-piperidinyl and 1-piperazinyl;

wherein the piperidinyl or piperazinyl is optionally substituted with —$C_{1-3}$alkyl-C(O)$NR^JR^K$; wherein $R^J$ and $R^K$ are each independently selected form hydrogen or $C_{1-4}$alkyl; alternatively, $R^J$ and $R^K$ are taken together with the nitrogen atom to which they are bound to form a 5 to 7 membered heterocycloalkyl;

or a pharmaceutically acceptable salt thereof.

4. A compound as in claim 3 wherein $R^1$ is hydrogen;

$A^1$ is —$CH_2$—;

$L^1$ is selected from the group consisting of —C(O)—N($CH_3$)—, —C(O)—NH—, and —NH—C(O)—;

$R^2$ is selected from the group consisting of t-butyl, cyclohexyl, 2-adamantyl and 4-(1-methyl-piperidinyl);

alternatively, $L^1$ is —C(O)—N($R^C$) and $R^C$ and $R^2$ are taken together with the nitrogen atom to which they are bound to form 1-(4-morpholinyl-carbonyl-methyl)-piperazinyl;

or a pharmaceutically acceptable salt thereof.

5. A compound as in claim 4, selected from the group consisting of 3-(2-Amino-6-phenoxy-3,4-dihydro-quinolin-3-yl)-N-cyclohexyl-N-methyl-propionamide;

3-(R)-(2-Amino-6-phenoxy-3,4-dihydro-quinolin-3-yl)-N-cyclohexyl-N-methyl-propionamide; and 3-(S)-(2-Amino-6-phenoxy-3,4-dihydro-quinolin-3-yl)-N-cyclohexyl-N-methyl-propionamide;

or pharmaceutically acceptable salts thereof.

6. A pharmaceutical composition comprising a pharmaceutically acceptable carrier and a compound of claim 1.

* * * * *